United States Patent [19]

Murase et al.

[11] Patent Number: 4,497,817
[45] Date of Patent: Feb. 5, 1985

[54] 2-PHENYLIMIDAZO [2,1-b]BENZOTHIAZOLE DERIVATIVES

[75] Inventors: Kiyoshi Murase, Saitama; Toshiyasu Mase, Chiba; Kenichi Tomioka, Saitama, all of Japan

[73] Assignee: Yamanouchi Pharmaceutical Co., Ltd., Tokyo, Japan

[21] Appl. No.: 487,357

[22] Filed: Apr. 26, 1983

Related U.S. Application Data

[63] Continuation of Ser. No. 176,907, Aug. 11, 1980, abandoned.

[30] Foreign Application Priority Data

Aug. 21, 1979 [JP]  Japan ................................. 54-106438
Nov. 9, 1979 [JP]   Japan ................................. 54-145077
Nov. 16, 1979 [JP]  Japan ................................. 54-148441

[51] Int. Cl.³ .................. C07D 277/60; A61K 31/425
[52] U.S. Cl. ..................................... 548/150; 548/152; 548/153; 548/154
[58] Field of Search ............... 548/150, 151, 152, 154; 424/270

[56] References Cited

U.S. PATENT DOCUMENTS 4,080,339  3/1978  Acheson et al. ..................... 548/151
4,110,460  8/1978  Baetz .................................. 548/154
4,262,004  4/1981  Lipido ................................ 548/151

FOREIGN PATENT DOCUMENTS 1070139  5/1967  United Kingdom ............... 548/151

OTHER PUBLICATIONS

C.A. 65, 7164(A) 1966.
C.A. 83, 164112(R) 1975.

Primary Examiner—Nicholas S. Rizzo
Attorney, Agent, or Firm—Burgess, Ryan & Wayne

[57] ABSTRACT

A novel 2-phenylimidazo[2,1-b]benzothiazole derivative shown by the following formula

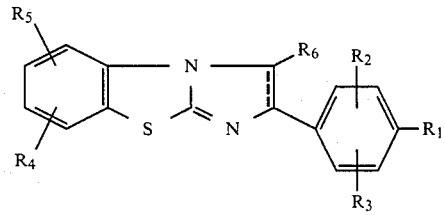

or a salt thereof which possesses an immunoregulatory action and is useful as an antiallergic agent, an antiasthmatic, and a suppressant of rejection at tissue transplantation and skin graft.

11 Claims, No Drawings

2-PHENYLIMIDAZO [2,1-b]BENZOTHIAZOLE DERIVATIVES

This application is a continuation, of application Ser. No. 176,907, filed Aug. 11, 1980, now abandoned.

DETAILED DESCRIPTION OF THE INVENTION

This invention relates to novel 2-phenylimidazo[2,1-b]benzothiazole derivatives. More particularly, the invention relates to the 2-phenylimidazo[2,1-b]benzothiazole derivatives shown by formula I

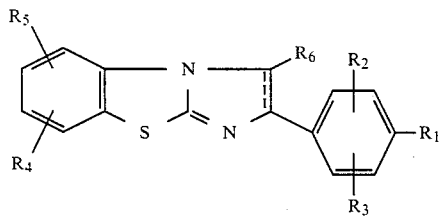

wherein $R_1$, $R_2$, and $R_3$, which may be the same or different, each represents a hydrogen atom, a halogen atom, a hydroxy group, a nitro group, a nitroso group, an amino group, a carboxy group, a nitrile group, a carbamoyl group, a sulfamoyl group, a lower alkyl group, a hydroxy lower alkyl group, a lower alkoxy group, a phenyl lower alkoxy group, a carboxy lower alkoxy group, a lower alkoxycarbonyl lower alkoxy group, a lower alkoxycarbonyl group, an acyloxy group, a lower alkylthio group, a lower alkylsulfinyl group, a lower alkylsulfonyl group, a lower alkoxysulfinyl group, a lower alkoxysulfonyl group, a mono or di lower alkylamino group, or an acylamino group; two adjacent ones of $R_1$, $R_2$, and $R_3$ may combine with each other to form a benzene ring or a lower alkylenedioxy group; $R_4$, $R_5$, and $R_6$, which may be the same or different, each represents a hydrogen atom, a halogen atom, a hydroxy group, a nitro group, a nitroso group, an amino group, a thiocyanate group, a lower alkyl group, a hydroxy lower alkyl group, a lower alkoxy group, a carboxy lower alkoxy group, a lower alkoxycarbonyl lower alkoxy group, an acyloxy group, a lower alkylthio group, a lower alkylsulfinyl group, a lower alkylsulfonyl group, a mono or di lower alkylamino group, an acylamino group or a group shown by formula

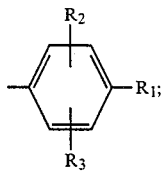

and the dotted line means the existence or absence of a double bond; however, when $R_2$, $R_3$, and $R_4$ all are a hydrogen atom, $R_5$ is a hydrogen atom, a halogen atom, a nitro group, a lower alkyl group or a lower alkoxy group, the dotted line signifies the existence of a double bond, and (1) $R_6$ is a hydrogen atom, $R_1$ represents the above groups other than a hydrogen atom, a fluorine atom, a chlorine atom, a bromine atom, a nitro group, a lower alkyl group or a lower alkoxy group; and (2) $R_6$ is a bromine atom or a thiocyanate group, $R_1$ represents the above groups other than a hydrogen atom or a halogen atom; and (3) $R_6$ is a nitroso group or a nitro group; $R_1$ represents the above groups other than a hydrogen atom or a nitro group, and a salt thereof.

By the term "lower" in general formula I described above is meant a straight or branched carbon chain having 1-5 carbon atoms. Therefore, the lower alkyl moiety of the lower alkyl group, hydroxy lower alkyl group, mono or di lower alkylamino group, lower alkylthio group, lower alkylsulfinyl group, lower alkylsulfonyl group shown by $R_1$, $R_2$, $R_3$, $R_4$, $R_5$ and $R_6$ is practically a methyl group, an ethyl group, a propyl group, an isopropyl group, a butyl group, a sec-butyl group, a tertbutyl group, etc. Also, the lower alkoxy moiety of the lower alkoxy group, phenyl lower alkoxy group, carboxy lower alkoxy group, lower alkoxycarbonyl lower alkoxy group, and lower alkoxycarbonyl group is practically a methoxy group, an ethoxy group, a propoxy group, a butoxy group, etc.

Also, as the acyl moiety of the acylamino group and acyloxy group, there are a lower alkanoyl group such as a formyl group, acetyl group, propionyl group, butyryl group, etc., an aromatic acyl group such as a benzoyl group, 4-methylbenzoyl group, etc., as well as an ethoxycarbonyl group, a methoxalyl group (—COCOOCH$_3$), an ethoxalyl group (—COCOOC$_2$H$_5$), an oxalo group (—COCOOH), a carbamoyl group, a tetrazol-5-ylcarbonyl group, a methanesulfonyl group, an ethanesulfonyl group, etc.

As halogen atoms, there are illustrated a fluorine atom, chlorine atom, iodine atom, bromine atom.

Furthermore, as the alkylenedioxy group formed by combining any two adjacent ones of $R_1$, $R_2$ and $R_3$, there are a methylenedioxy group, an ethylenedioxy group, etc.

The compounds of the above-shown general formula I provided by this invention form acid addition salts or form, according to the kind of substituents, salts with bases. This invention includes the pharmaceutically acceptable salts of the compounds of general formula I and examples of these salts are acid addition salts with a mineral acid such as hydrochloric acid, hydrobromic acid, nitric acid, sulfuric acid, etc., or an organic acid such as methanesulfonic acid, p-toluenesulfonic acid, etc. As the salts with bases formed according to the kind of the substituent in general formula I, there are the salts with alkali metals such as sodium, potassium, etc., or alkaline earth metals such as calcium, etc.; the salts with ammonia; and the salts with organic bases such as methylamine, ethylamine, diethylamine, trimethylamine, triethylamine, pyridine, picoline, arginine, lysine, etc.

Hitherto, as 2-phenylimidazo[2,1-b]benzothiazole derivatives, for example, the following compounds are known. That is, there are 2-phenylimidazo[2,1-b]benzothiazole (Chem. Abstr., 34, 5082$^3$(1940)), 2-(4-bromophenyl, 4-chlorophenyl or 4-fluorophenyl)imidazo[2,1-b]benzothiazole, 2-(4-chlorophenyl or phenyl)-7-(ethoxy, methoxy or methyl)imidazo[2,1-b]benzothiazole (Chem. Abstr., 65, 7164a(1966)), 2-(4-nitrophenyl)imidazo[2,1-b]benzothiazole, 2-(4-nitrophenyl)-3-nitroimidazo[2,1-b]benzothiazole, 2-phenyl-3-nitroso-imidazo[2,1-b]benzothiazole (Chem. Abstr., 68, 95754g(1968)), 2-(4-nitrophenyl or phenyl)-3-(nitro or nitroso)-5,6,7 or 8-(methoxy or methyl)imidazo[2,1-b]benzothiazole, 2-(4-nitrophenyl or phenyl)-5,6,7 or 8-(methoxy or methyl)imidazo[2,1-b]benzothiazole (Chem. Abstr., 71, 124309t(1969)), 2-(4-methoxyphenyl)imidazo[2,1-b]benzothiazole (Chem. Abstr., 72, 100606g(1970)), 2-(4-bromophenyl, 4-chlorophenyl or phenyl)-3-(bromo or thiocyanato)imidazo[2,1-b]benzothiazole (Chem. Abstr., 77, 114304x(1972)), 2-(4-biphenyl or 4-methylphenyl)imidazo[2,1-b]benzothiazole, 2-(4-biphenyl, 4-methoxyphenyl, 4-methylphenyl, 4-nitrophenyl or phenyl)-7-(bromo, ethoxy, methoxy, methyl or nitro)imidazo[2,1-b]benzothiazole (Chem. Abstr., 77, 164598s(1972)). However, there are no disclosures in these of these compounds as medicaments.

J, Indian Chemical Soc., 51 (12), 1031(1974) (Chem. Abstr., 83, 164112c(1975)) discloses that the 2-phenylimidazo[2,1-b]benzothiazole derivatives shown by the formula

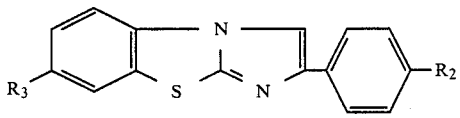

wherein $R_2$ is Cl, Ph, OMe, OEt, or Br and $R_3$ is H, Me or Cl have been confirmed to possess a fungicidal activity but not to possess an antihistamic activity. That is, various 2-phenylimidazo[2,1-b]benzothiazole derivatives are known as described above but it had not been known that compounds of this kind were effective to an immunity system and possessed a strong immunoregulatory action.

On the other hand, the compounds of this invention possess an immunoregulatory action and are useful as antiallergic agents, antiasthmatics, and suppressants of rejection at tissue transplantation and skin graft.

The compounds of this invention have an immunoregulatory action but are characterized as having an immunosuppressive action and an immunostimulating action.

The compounds of this invention having an immunosuppressive action which possess the action of suppressing cell-mediated immunity, for example suppressiving a delayed type hypersensitivity reaction typified by the cell-mediated immunity to protein antigens are useful as an antiallergic agent, an antirheumatic, a therapeutic agent of autoimmune disease, and a suppressant of rejection at the tissue transplantation and skin graft. In particular, these compounds are useful as a delayed type hyerpsensitive agent and antirheumatics. That is, hitherto, steroids only are known as antiallergic agents, in particular a delayed type hypersensitive agent. The same is true as antirheumatics. However, when steroids are used for a long period of time, they cause a serious side action and cause a so-called steriod reliance and hence it has been desired to develop a non-steriod type antiallergic and antirheumatic agent giving less side rections. The compounds of this invention having a strong delayed type hypersensitive action can be used in place of these steroids. Further, they can be used together with the steroids, thereby reducing amount of steroids.

The compounds of this invention having an immunosuppressive action and also having a suppression of humoral antibody formation, e.g., an action of suppressing the production of IgE antibody, are useful as antiallergic agents since they suppress the production of IgE antibody which is the main cause of immediate hypersensitivity.

The compounds of this invention having an immunostimulating action and having an action of increasing cell-mediated immunity such as the action of increasing a delayed type hypersensitivity reaction as well as having an action of lymphocyte blastogenesis, and an action of increasing humoral antibody formation, such as the action of increasing antibodies in blood are useful and a therapeutic agent of chronic hepatitis.

The compounds of this invention exhibit a suppressive action in a passive cutaneous anaphylaxises (PCA) test, which means the compounds of this invention have an antiallergic action and are useful as an antiallergic agent and an antiasthmatic.

Furthermore, since the compounds of this invention show very low toxicity, the compounds can be used as medicaments for various uses above described.

The medical compositions containing the compounds of this invention as the main component are formulated by a conventional manner using conventional carriers for formulation and excipients. The medicaments may be administered orally as tablets, pills, capsules, granules, etc., or may be administered parenterally as injections such as intravenous injections, intramuscular injections, etc., or as aerosols, suppositories, etc. The doeses of the medicaments are properly determined according to each case on considering the symptom, the age of patient, sex distinction, etc., but are usually 50-500 mg per day for adults in case of oral administration and 20-300 mg per day for adults in case of parenteral administration, which is administered in 2-3 times a day.

The compounds of this invention are prepared by any one of the following methods.

(A) Cyclization:

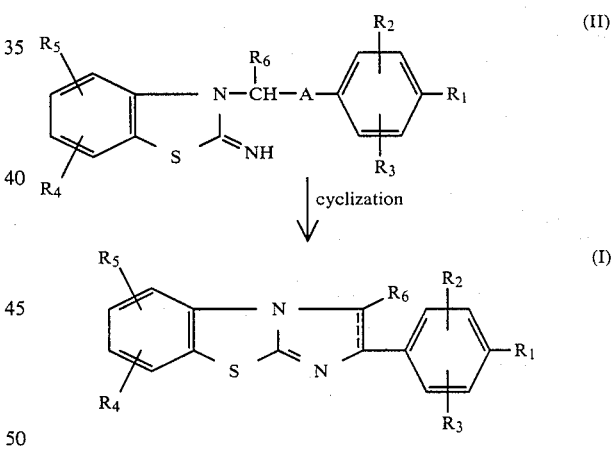

wherein A represents a carbonyl group or a group shown by

(wherein Y represents a halogen atom).

Examples of the halogen atoms shown by Y are iodine atom, bromine atom, chlorine atom, etc.

In the above reaction, a starting material is used wherein A is a carbonyl group and a reaction using as the starting material a compound wherein A is an

group. That is, in the case of preparing the 2-phenylimidazo[2,1-b]benzothiazole derivative shown by general formula (Ia)

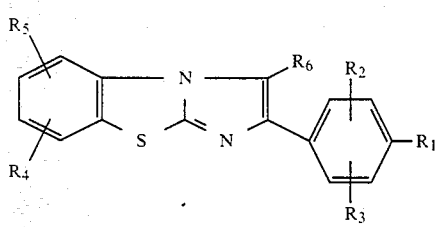

the compound (IIa) wherein A is a carbonyl group is used as the starting material, while in the case of preparing the 2-phenyl-2,3-dihydroimidazo[2,1-b]benzothiazole derivatives shown by general formula (Ib)

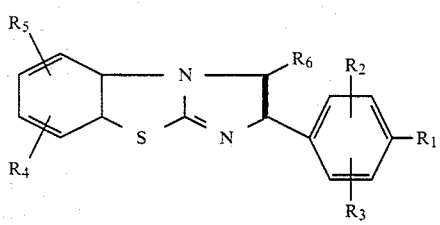

the compound (IIb) wherein A is the group shown by

is used as the starting material.

The former reaction is usually performed in a solvent and as the solvent employed in this case, there are, for example, methanol, ethanol, isopropanol, methoxyethanol, methylcellosolve, ethylcellosolve, Diglyme, ethyl acetate, acetonitrile, chloroform, carbon tetrachloride, etc. The reaction is performed under heating, preferably under refluxing.

On the other hand, the latter reaction is performed usually in a solvent in the presence of a base under heating, preferably under refluxing. Examples of a suitable solvent are, for example, organic solvents such as alcohols (methanol, ethanol, etc.) chloromethane, dichloromethane, chloroform, carbon tetrachloride, methylcellosolve, ethylcellosolve, Diglyme, ethyl acetate, acetonitrile, etc., and water or mixtures thereof. As the base used in the reaction, there are inorganic bases such as potassium carbonate, sodium carbonate, sodium hydrogencarbonate, potassium acetate, sodium acetate, etc., and organic bases scuh as trimethylamine, triethylamine, pyridine, picoline, etc. Pyridine, etc., may be also used as solvents.

In this case, when the starting material (II) wherein at least one of $R_1$ to $R_6$ is an acyloxy group is used, it is hydrolyzed during the reaction to form the corresponding compound (I) of this invention wherein at least one of $R_1$ to $R_6$ is a hydroxy group.

In addition, starting materials (IIa) and (IIb) are produced according to the following reaction formulae and they can be used in the reactions without being isolated.

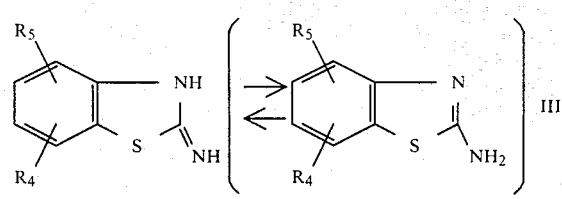

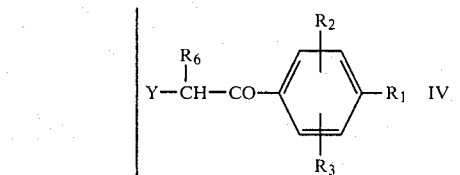

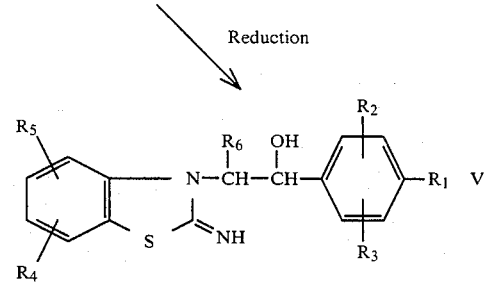

Reduction

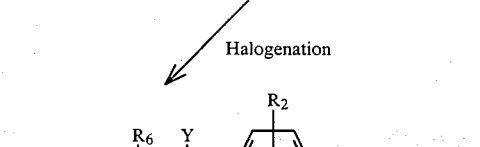

Halogenation

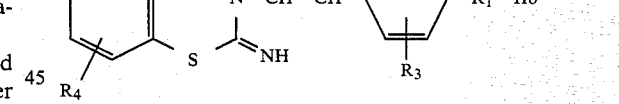

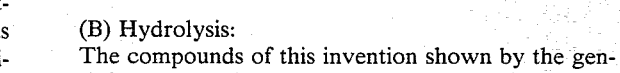

(B) Hydrolysis:

The compounds of this invention shown by the general formula (I) having a hydroxy group, a carboxy group, or an amino group can be prepared by hydrolyzing the compounds having an acyloxy group, a lower alkoxycarbonyl group, or an acylamino group in an ordinary manner. That is, a compound of formula (I) wherein at least one of $R_1$ to $R_6$ is a hydroxy group can be prepared by hydrolyzing a compound of formula (I) wherein at least one of $R_1$ to $R_6$ is an acyloxy group under alkaline conditions in a conventional manner; the compounds of formula (I) wherein at least one of $R_1$ to $R_3$ is a carboxy group or a carboxy lower alkoxy group can be prepared by hydrolyzing a compound wherein at least one of $R_1$ to $R_3$ is a lower alkoxycarbonyl group or a lower alkoxycarbonyl lower alkoxy group under alkaline conditions in a conventional manner; and the compounds of formula (I) wherein at least one of $R_4$ to $R_6$ is a carboxy lower alkoxy group can be prepared by hydrolyzing a compound wherein at least one of $R_4$ to $R_6$ is a lower alkoxycarbonyl lower alkoxy group under alkaline conditions in a conventional manner. Also, the compounds of formula (I) wherein at least one of $R_1$ to $R_6$ is an acylamino group containing a carboxy group, such as an oxaloamido group (—NHCOCOOH) can be prepared by hydrolyzing a compound having a lower alkoxycarbonyl group, e.g., a compound having an ethoxyalylamido group (—NHCOCOOC$_2$H$_5$) under alkaline conditions in a conventional manner. Furthermore, the compounds of formula (I) wherein at least one of $R_1$ to $R_6$ is an amino group can be prepared by hydrolyzing a compound wherein at least one of $R_1$ to $R_6$ is an acylamino group under acid conditions in a conventional manner.

(C) Alkylation:

The compounds of this invention shown by the general formula (I) having a lower alkoxy group, a phenyl lower alkoxy group, a lower alkoxycarbonyl lower alkoxy group, a lower alkylenedioxy group, a lower alkoxycarbonyl group, or a mono or di lower alkylamino group can be prepared by alkylating a compound having a hydroxy group, a carboxy group, or an amino group by reacting the compound with a corresponding alkylating agent in an a conventional manner. That is, the compounds of formula (I) wherein at least one of $R_1$ to $R_6$ is a lower alkoxy group or a lower alkoxycarbonyl lower alkoxy group can be prepared by alkylating a compound wherein at least one of $R_1$ to $R_6$ is a hydroxy group with a corresponding alkylating agent such as a lower alkyl halide or a lower alkoxycarbonylalkyl halide in a conventional manner; the compounds wherein at least one of $R_1$ to $R_3$ is a phenyl lower alkoxy group can be prepared by alkylating a compound wherein at least one of $R_1$ to $R_3$ is hydroxy group with a corresponding alkylating agent such as a phenyl lower alkyl halide in a conventional manner; and the compounds wherein optional adjacent two groups of $R_1$ to $R_3$ are combined with each other to form a lower alkylenedioxy group can be prepared by alkylating a compound wherein two groups of $R_1$ to $R_3$ are hydroxy groups with a corresponding alkylating agent such as a lower alkylene dihalide in a conventional manner. Also, the compounds of this invention shown by formula (I) wherein at least one of $R_4$ to $R_6$ is a lower alkoxycarbonyl group can be prepared by alkylating a compound wherein at least one of $R_4$ to $R_6$ is a carboxy group by reacting a compound with a corresponding alkylating agent such as a lower alkyl halide in a convnetional manner and the compounds of formula (I) wherein at least one of $R_1$ to $R_6$ is a lower alkoxycarbonyl lower alkoxy group can be prepared by alkylating a compound wherein at least one of $R_1$ to $R_6$ is a carboxy lower alkoxy group with a corresponding alkylating agent in a conventional manner. Furthermore, the compounds of formula (I) wherein at least one of $R_1$ to $R_6$ is a mono or di lower alkylamino group can be prepared by alkylating a compound wherein at least one of $R_1$ to $R_6$ is an amino group with a corresponding alkylating agent such as a lower alkyl halide in a conventional manner.

(D) Acylation:

The compounds of this invention having the general formula (I) wherein at least one of $R_1$ to $R_6$ is an acyloxy group or an acylamino group can be prepared by acylating a compound wherein at least one of $R_1$ to $R_6$ is a hydroxy group or an amino group with a corresponding acylating agent such as an acyl halide, acid anhydride in a conventional manner.

(E) Amide formation:

The compound of this invention of general formula (I) having carbamoyl group(s) can be prepared by amide-forming a compound having a carboxy group or a lower alkoxycarbonyl group in a conventional manner. That is, the compound of formula (I) wherein at least one of $R_4$ to $R_6$ is a carbamoyl group can be prepared by reacting a compound wherein at least one of $R_4$ to $R_6$ is a carboxy group or a lower alkoxycarbonyl group with ammonia in a conventional manner and the compounds of formula (I) wherein at least one of $R_1$ to $R_6$ is an acylamino group having a carbamoyl group, e.g., a compound having an oxamido group (—NHCOCONH$_2$) can be prepared by reacting a conventional compound wherein at least one of $R_1$ to $R_6$ is an acylamino group having a carboxy group or lower alkoxycarbonyl group, such as an ethoxalylamido group (—NHCOCOOC$_2$H$_5$) with ammonia in a conventional manner.

(F) Halogenation:

The compounds of this invention having the general formula (I) wherein $R_6$ is a halogen atom can be prepared by halogenating a compound of formula (I) wherein $R_6$ is a hydrogen atom with a halogenating agent such as bromine, chlorine, iodine, sulfuryl chloride, and N-bromosuccinic acid imide in a conventional manner.

(G) Nitration:

The compounds of this invention having the general formula (I) wherein $R_6$ is a nitro group can be prepared by nitrating the compound of formula (I) wherein $R_6$ is a hydrogen atom by reacting the compound with a nitrating agent such as nitric acid in a conventional manner.

(H) Nitroso formation:

The compounds of this invention having the general formula (I) wherein $R_6$ is a nitroso group can be prepared be reacting a compound of formula (I) wherein $R_6$ is a hydrogen atom with a nitroso-forming agent such as nitrous acid in a conventional manner.

(I) Reduction:

The compounds of this invention having the general formula (I) having an amino group or a hydroxy lower alkyl group can be prepared by reducing a compound of formula (I) having a nitro group, a lower alkanoyl group, or a lower alkoxycarbonyl group in a conventional manner. That is, the compounds of formula (I) wherein at least one of $R_1$ to $R_6$ is an amino group can be prepared by reducing a compound wherein at least one of $R_1$ to $R_6$ is a nitro group in a conventional ordinary manner and the compounds of formula (I) wherein at least one of $R_1$ to $R_6$ is a hydroxy lower alkyl group can be prepared by reducing the compound wherein at least one of $R_1$ to $R_6$ is a lower alkanoyl group or a lower alkoxycarbonyl group in a conventional manner.

(J) Lower alkylthio formation:

The compounds of this invention having the general formula (I) wherein $R_6$ is a lower alkylthio group can be prepared by reacting a compound of formula (I) wherein $R_6$ is a hydrogen atom with a lower alkylthio forming agent such as a lower alkylsulfinyl halide in a conventional manner.

(K) Oxidation:

The compound of this invention having general formula (I) wherein at least one of $R_1$ to $R_6$ is a lower alylsulfinyl group or a lower alkylsulfonyl group can be prepared by oxidizing a compound of formula (I) wherein at least one of $R_1$ to $R_6$ is a lower alkylthio group in a conventional manner.

The desired compounds of formula (I) thus prepared are isolated and purified by a conventional chemical operation usually used in the field of the art, such as recrystallization, extraction, various chromatographies, etc.

Then, the experimental results indicating the excellent pharmacological effects of the compounds of this invention are shown below.

Activity to delayed type hypersensitivity of mice:

Seven week old ICR-SLC mice (Shizuoka Agric. Coop. Asoc.) were sensitized by painting 0.1 ml of 7% picryl chloride (PC) solution in absolute ethanol on the shaved abdomen. In this case, the solution was used under heating for preventing PC from being precipitated. After the 7 day sensitization period, the mice were challenged by painting 0.02 ml of 1% picryl chloride solution in olive oil on inside of each ear. The ear thickness was measured with a dial thickness gauze. Increase in ear thickness was calculated as a difference between the value measured before challenge and after 24 hours since then. The test compounds were administered orally from day 0 to day 3 after the immunization. The results are shown in Table I.

| Drug | Dose (mg/kg) | N | Ear thickness increment (1/100 mm) | Inhibition (%) |
|---|---|---|---|---|
| 2-(m-Hydroxyphenyl)imidazo[2,1-b]benzothiazole (Ex. 8) | 50 | 5 | 3.4 ± 0.9 | 39.3 |
|  | 400 | 5 | 0.9 ± 0.4 | 83.9 |
| Control | — | 10 | 5.6 ± 0.6 | — |
| 7-Hydroxy-2-(p-methoxyphenyl)imidazo[2,1-b]-benzothiazole (Ex. 23) | 50 | 5 | 2.0 ± 0.8 | 53.5 |
|  | 400 | 5 | 2.2 ± 0.7 | 48.8 |
| Control | — | 10 | 4.3 ± 0.7 | — |
| 7-Hydroxy-2-(p-hydroxyphenyl)imidazo[2,1-b]benzothiazole hemihydrate (Ex. 24) | 50 | 5 | 2.4 ± 0.6 | 44.2 |
|  | 400 | 5 | 2.5 ± 0.8 | 41.9 |
| Control | — | 10 | 4.3 ± 0.7 | — |
| 7-Hydroxy-2-phenylimidazo[2,1-b]benzothiazole (Ex. 25) | 50 | 5 | 2.5 ± 0.2 | 41.9 |
|  | 400 | 5 | 2.4 ± 0.7 | 44.2 |
| Control | — | 10 | 4.3 ± 0.7 | — |
| 2-(3-Chloro-4-hydroxyphenyl)imidazo[2,1-b]benzothiazole (Ex. 28) | 50 | 5 | 3.4 ± 1.1 | 35.8 |
|  | 400 | 5 | 2.7 ± 0.5 | 48.6 |
| Control | — | 10 | 5.3 ± 0.5 | — |
| 2-(3,5-Dichloro-4-hydroxyphenyl)imidazo[2,1-b]benzothiazole (Ex. 29) | 50 | 5 | 3.4 ± 0.7 | 35.8 |
|  | 400 | 5 | 1.3 ± 0.6 | 75.2 |
| Control | — | 10 | 5.3 ± 0.5 | — |
| 2-(3-Hydroxy-4-methylphenyl)imidazo[2,1-b]benzothiazole (Ex. 30) | 50 | 5 | 3.3 ± 1.3 | 37.7 |
|  | 400 | 5 | 3.2 ± 1.0 | 39.6 |
| Control | — | 10 | 5.3 ± 0.5 | — |
| 2-(4-Chloro-3-hydroxyphenyl)imidazo[2,1-b]benzothiazole (Ex. 32) | 50 | 5 | 2.4 ± 0.9 | 44.2 |
| Control | — | 10 | 4.3 ± 0.7 | — |
| 2-(m-Nitrophenyl)imidazo[2,1-b]benzothiazole (Ex. 33) | 50 | 5 | 3.2 ± 0.4 | 39.0 |
|  | 400 | 5 | 2.1 ± 0.5 | 60.0 |
| Control | — | 10 | 5.3 ± 0.5 | — |
| 2-(m-Methoxycarbonylphenyl)imidazo[2,1-b]benzothiazole (Ex. 36) | 50 | 5 | 1.9 ± 0.7 | 63.8 |
|  | 400 | 5 | 1.9 ± 0.5 | 63.8 |
| Control | — | 10 | 5.3 ± 0.5 | — |
| 3-Methyl-2-phenylimidazo[2,1-b]benzothiazole (Ex. 41) | 50 | 5 | 3.9 ± 0.7 | 31.6 |
|  | 400 | 5 | 3.7 ± 0.8 | 35.1 |
| Control | — | 10 | 5.7 ± 0.5 | — |
| 2,3-Bis(p-chlorophenyl)-imidazo[2,1-b]benzothiazole (Ex. 46) | 400 | 5 | 2.0 ± 0.6 | 63.6 |
| Control | — | 10 | 5.5 ± 0.4 | — |
| 2-(o-Hydroxyphenyl)imidazo[2,1-b]benzothiazole (Ex. 50) | 400 | 5 | 1.4 ± 0.2 | 65.0 |
| Control | — | 10 | 4.0 ± 0.5 | — |
| 2-(p-Hydroxyphenyl)imidazo[2,1-b]benzothiazole (Ex. 54) | 50 | 5 | 3.4 ± 0.8 | 44.3 |
|  | 400 | 5 | 3.6 ± 0.4 | 41.0 |
| Control | — | 10 | 6.1 ± 0.7 | — |
| 2-(p-Carboxyphenyl)imidazo[2,1-b]benzothiazole (Ex. 60) | 50 | 5 | 3.8 ± 0.7 | 33.3 |
|  | 400 | 5 | 2.9 ± 0.6 | 49.1 |
| Control | — | 10 | 5.7 ± 0.5 | — |
| 2-(m-Formamidophenyl)imidazo[2,1-b]benzothiazole (Ex. 72) | 25 | 5 | 2.6 ± 0.7 | 39.5 |
|  | 200 | 5 | 2.2 ± 1.1 | 48.8 |
| Control | — | 10 | 4.3 ± 0.7 | — |
| 2-(p-Chlorophenyl)-3-nitrosoimidazo[2,1-b]benzothiazole (Ex. 90) | 400 | 5 | 2.9 ± 0.3 | 47.3 |
| Control | — | 10 | 5.5 ± 0.4 | — |

EXAMPLE 1

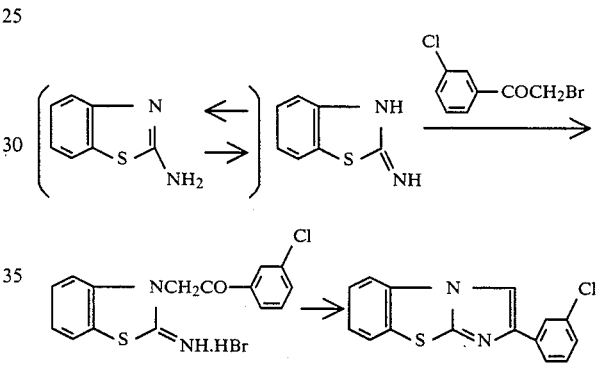

To 150 ml of anhydrous acetonitrile were added 4.5 g of 2-aminobenzothiazole and 6.8 g of m-chlorphenacyl bromide and the mixture was heated to 65°–75° C. for one hour with stirring. After the reaction was over, the reaction mixture was cooled, crystals formed were recovered by filtration, washed with acetonitrile, and dried to provide 8.5 g of the white crystals of 2-imino-3-(m-chlorobenzoylmethyl)-2,3-dihydrobenzothiazole hydrobromide.

Then, 8.5 g of the crystals of the hydrobromide were refluxed under heating in 75 ml of methylcellosolve. After the reaction was over, the reaction mixture was cooled to about 50° C. and then 30 ml of 5% aqueous ammonia was added to the reaction mixture, thereby white crystals formed. The reaction mixture was further ice-cooled and crystals formed were recovered by filtration and recrystallized from ethanol to provide 4.2 g of 2-(m-chlorophenyl)imidazo[2,1-b]benzothiazole.

Melting point: 173°–175° C.

| Elemental analysis for $C_{15}H_9N_2ClS$: | | | | |
|---|---|---|---|---|
|  | C (%) | H (%) | N (%) | S (%) |
| Calculated: | 63.27 | 3.19 | 9.84 | 11.26 |
| Found: | 63.17 | 3.03 | 9.68 | 11.48 |

By following the same general procedures as above, but using the corresponding starting materials, the following compounds were prepared.

EXAMPLE 2

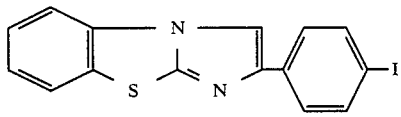

2-(p-Iodophenyl)imidazo[2,1-b]benzothiazole
melting point
177–180° C.

Elemental analysis for $C_{15}H_9N_2IS$:

|  | C (%) | H (%) | N (%) | S (%) |
|---|---|---|---|---|
| Calculated: | 47.89 | 2.41 | 7.45 | 8.52 |
| Found: | 48.12 | 2.43 | 7.34 | 8.28 |

EXAMPLE 3

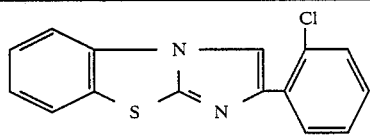

2-(o-Chlorophenyl)imidazo[2,1-b]benzothiazole
melting point
178–179° C.

Elemental analysis for $C_{15}H_9N_2ClS$:

|  | C (%) | H (%) | N (%) | S (%) |
|---|---|---|---|---|
| Calculated: | 63.27 | 3.19 | 9.84 | 11.26 |
| Found: | 63.05 | 2.98 | 9.70 | 11.56 |

EXAMPLE 4

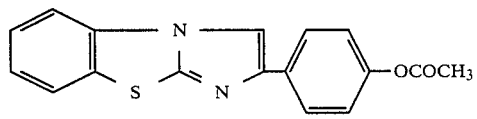

2-(p-Acetoxyphenyl)imidazo[2,1-b]benzothiazole
melting point
177–179° C.

Elemental analysis for $C_{17}H_{12}N_2O_2S$:

|  | C (%) | H (%) | N (%) | S (%) |
|---|---|---|---|---|
| Calculated: | 66.22 | 3.92 | 9.08 | 10.40 |
| Found: | 66.19 | 3.74 | 9.01 | 10.52 |

EXAMPLE 5

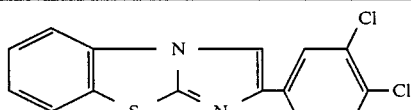

2-(3,4-Dichlorophenyl)imidazo[2,1-b]benzothiazole
melting point
195–197° C.

Elemental analysis for $C_{15}H_8N_2Cl_2S$:

|  | C (%) | H (%) | N (%) | S (%) | Cl (%) |
|---|---|---|---|---|---|
| Calculated: | 56.44 | 2.53 | 8.78 | 10.04 | 22.21 |
| Found: | 56.52 | 2.40 | 8.80 | 10.17 | 22.13 |

EXAMPLE 6

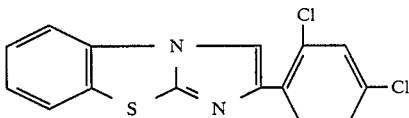

2-(2,4-Dichlorophenyl)imidazo[2,1-b]benzothiazole
melting point
198–199° C.

Elemental analysis for $C_{15}H_8N_2Cl_2S$:

|  | C (%) | H (%) | N (%) | S (%) | Cl (%) |
|---|---|---|---|---|---|
| Calculated: | 56.44 | 2.53 | 8.78 | 10.04 | 22.21 |
| Found: | 56.48 | 2.55 | 8.80 | 10.21 | 21.91 |

EXAMPLE 7

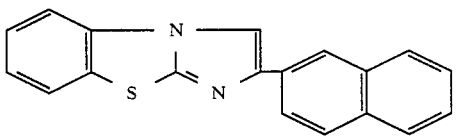

2-(2-Naphthyl)imidazo[2,1-b]benzothiazole
melting point
161–163° C.

Elemental analysis for $C_{19}H_{12}N_2S$:

|  | C (%) | H (%) | N (%) | S (%) |
|---|---|---|---|---|
| Calculated: | 75.97 | 4.03 | 9.33 | 10.67 |
| Found: | 76.12 | 3.89 | 9.28 | 10.77 |

EXAMPLE 8

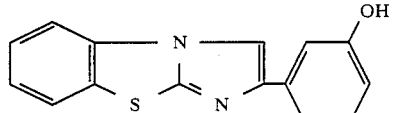

2-(m-Hydroxyphenyl)imidazo[2,1-b]benzothiazole
melting point
248° C.

Elemental analysis for $C_{15}H_{10}N_2OS$:

|  | C (%) | H (%) | N (%) | S (%) |
|---|---|---|---|---|
| Calculated: | 67.65 | 3.78 | 10.52 | 12.04 |
| Found: | 67.47 | 3.76 | 10.32 | 12.17 |

EXAMPLE 9

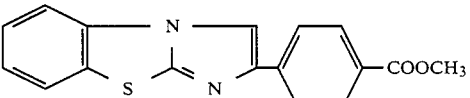

2-(p-Methoxycarbonylphenyl)imidazo[2,1-b]benzothiazole
melting point
223° C.

Elemental analysis for $C_{17}H_{12}N_2O_2S$:

|  | C (%) | H (%) | N (%) | S (%) |
|---|---|---|---|---|
| Calculated: | 66.22 | 3.92 | 9.08 | 10.40 |
| Found: | 66.03 | 3.85 | 8.89 | 10.36 |

EXAMPLE 10

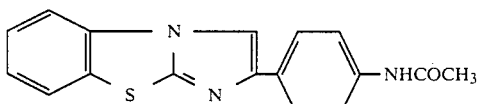

2-(p-Acetamidophenyl)imidazo[2,1-b]benzothiazole
melting point
243–245° C.
Elemental analysis for $C_{17}H_{13}N_3OS$:

|  | C (%) | H (%) | N (%) | S (%) |
|---|---|---|---|---|
| Calculated: | 66.43 | 4.26 | 13.67 | 10.43 |
| Found: | 66.21 | 4.20 | 13.46 | 10.50 |

EXAMPLE 11

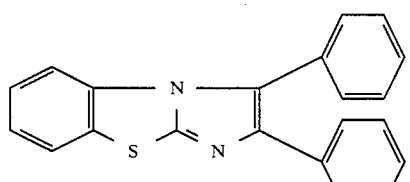

2,3-Diphenylimidazo[2,1-b]benzothiazole
melting point
161–162° C.
Elemental analysis for $C_{21}H_{14}N_2S$:

|  | C (%) | H (%) | N (%) | S (%) |
|---|---|---|---|---|
| Calculated: | 77.27 | 4.32 | 8.58 | 9.82 |
| Found: | 77.09 | 4.18 | 8.46 | 9.76 |

EXAMPLE 12

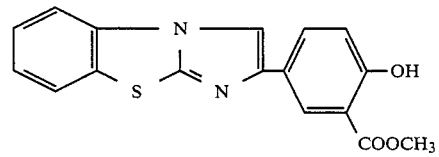

2-(4-Hydroxy-3-methoxycarbonylphenyl)imidazo[2,1-b]benzothiazole
melting point
224–226° C.
Elemental analysis for $C_{17}H_{12}N_2O_3S$:

|  | C (%) | H (%) | N (%) | S (%) |
|---|---|---|---|---|
| Calculated: | 62.95 | 3.73 | 8.64 | 9.88 |
| Found: | 63.20 | 3.60 | 8.33 | 9.98 |

EXAMPLE 13

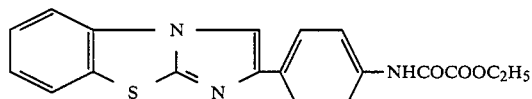

2-[p-(Ethoxalylamido)phenyl]imidazo[2,1-b]benzothiazole
melting point
220° C.
Elemental analysis for $C_{19}H_{15}N_3O_3S$:

|  | C (%) | H (%) | N (%) | S (%) |
|---|---|---|---|---|
| Calculated: | 62.45 | 4.14 | 11.50 | 8.77 |
| Found: | 62.24 | 3.89 | 11.40 | 9.04 |

EXAMPLE 14

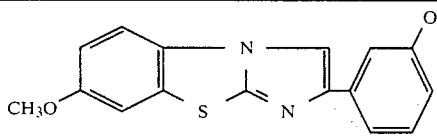

2-(m-Hydroxyphenyl)-7-methoxyimidazo[2,1-b]benzothiazole melting point 293–295° C.
Elemental analysis for $C_{16}H_{12}N_2O_2S$:

|  | C (%) | H (%) | N (%) | S (%) |
|---|---|---|---|---|
| Calculated: | 64.85 | 4.08 | 9.45 | 10.82 |
| Found: | 64.76 | 4.02 | 9.53 | 11.65 |

EXAMPLE 15

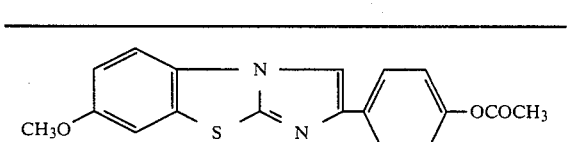

2-(p-Acetoxyphenyl)-7-methoxyimidazo[2,1-b]benzothiazole melting point 193–195° C.
Elemental analysis for $C_{18}H_{14}N_2O_3S$:

|  | C (%) | H (%) | N (%) | S (%) |
|---|---|---|---|---|
| Calculated: | 63.89 | 4.17 | 8.28 | 9.47 |
| Found: | 63.68 | 4.21 | 8.17 | 9.43 |

EXAMPLE 16

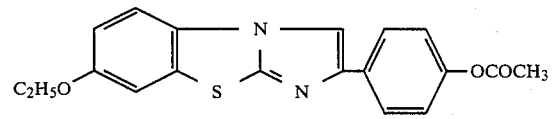

2-(p-Acetoxyphenyl)-7-ethoxyimidazo[2,1-b]benzothiazole melting point 186–188° C.
Elemental analysis for $C_{19}H_{16}N_2O_3S$:

|  | C (%) | H (%) | N (%) | S (%) |
|---|---|---|---|---|
| Calculated: | 64.76 | 4.58 | 7.95 | 9.10 |
| Found: | 65.01 | 4.49 | 7.80 | 9.11 |

EXAMPLE 17

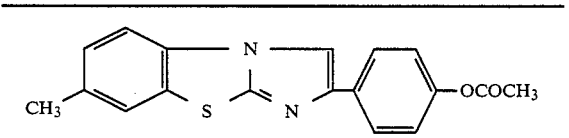

2-(p-Acetoxyphenyl)-7-methylimidazo[2,1-b]benzothiazole melting point 209° C.
Elemental analysis for $C_{18}H_{14}N_2O_2S$:

|  | C (%) | H (%) | N (%) | S (%) |
|---|---|---|---|---|
| Calculated: | 66.24 | 4.32 | 8.58 | 11.05 |
| Found: | 66.23 | 4.18 | 8.64 | 11.09 |

EXAMPLE 18

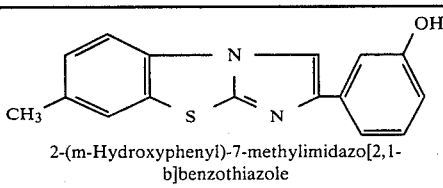

2-(m-Hydroxyphenyl)-7-methylimidazo[2,1-b]benzothiazole melting point above 300° C.
Elemental analysis for $C_{16}H_{12}N_2OS$:

|  | C (%) | H (%) | N (%) | S (%) |
| --- | --- | --- | --- | --- |
| Calculated: | 68.55 | 4.31 | 9.99 | 11.44 |
| Found: | 68.25 | 4.17 | 10.05 | 11.32 |

EXAMPLE 19

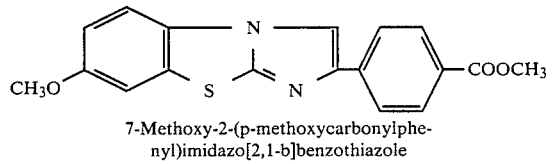

7-Methoxy-2-(p-methoxycarbonylphenyl)imidazo[2,1-b]benzothiazole melting point 215–217° C.
Elemental analysis for $C_{18}H_{14}N_2O_3S$:

|  | C (%) | H (%) | N (%) | S (%) |
| --- | --- | --- | --- | --- |
| Calculated: | 63.89 | 4.17 | 8.28 | 9.47 |
| Found: | 63.76 | 4.04 | 8.44 | 9.50 |

EXAMPLE 20

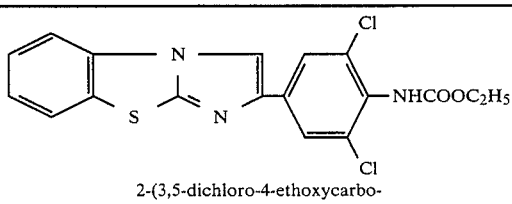

2-(3,5-dichloro-4-ethoxycarbonylamidophenyl)imidazo[2,1-b]benzothiazole melting point 256–258° C.
Elemental analysis for $C_{18}H_{13}N_3O_2Cl_2S$:

|  | C (%) | H (%) | N (%) | S (%) | Cl (%) |
| --- | --- | --- | --- | --- | --- |
| Calculated: | 53.21 | 3.22 | 10.34 | 7.89 | 17.45 |
| Found: | 53.05 | 3.12 | 10.34 | 7.79 | 17.28 |

EXAMPLE 21

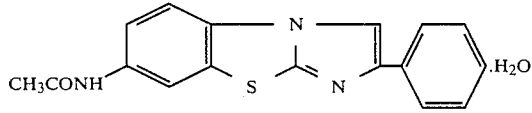

7-Acetamido-2-phenylimidazo[2,1-b]benzothiazole monohydrate melting point 267–269° C.
Elemental analysis for $C_{17}H_{15}N_3O_2S$:

|  | C (%) | H (%) | N (%) | S (%) |
| --- | --- | --- | --- | --- |
| Calculated: | 62.75 | 4.65 | 12.91 | 9.85 |

-continued

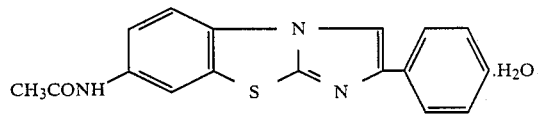

7-Acetamido-2-phenylimidazo[2,1-b]benzothiazole monohydrate melting point 267–269° C.
Elemental analysis for $C_{17}H_{15}N_3O_2S$:

|  | C (%) | H (%) | N (%) | S (%) |
| --- | --- | --- | --- | --- |
| Found: | 62.71 | 4.62 | 12.97 | 10.13 |

EXAMPLE 22

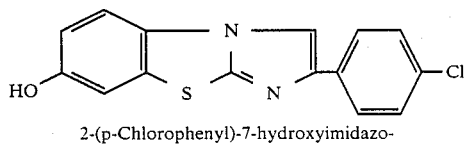

2-(p-Chlorophenyl)-7-hydroxyimidazo[2,1-b]benzothiazole melting point above 300° C.
Elemental analysis for $C_{15}H_9N_2OSCl$:

|  | C (%) | H (%) | N (%) | S (%) | Cl (%) |
| --- | --- | --- | --- | --- | --- |
| Calculated: | 59.90 | 3.02 | 9.31 | 10.66 | 11.79 |
| Found: | 59.80 | 2.92 | 9.25 | 10.52 | 12.00 |

EXAMPLE 23

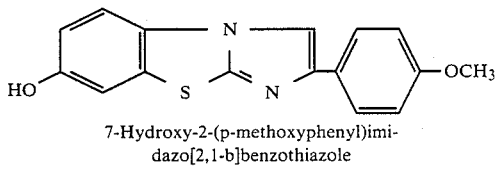

7-Hydroxy-2-(p-methoxyphenyl)imidazo[2,1-b]benzothiazole melting point 287–289° C.
Elemental analysis for $C_{16}H_{12}N_2O_2S$:

|  | C (%) | H (%) | N (%) | S (%) |
| --- | --- | --- | --- | --- |
| Calculated: | 64.85 | 4.08 | 9.45 | 10.82 |
| Found: | 64.83 | 4.01 | 9.41 | 10.69 |

EXAMPLE 24

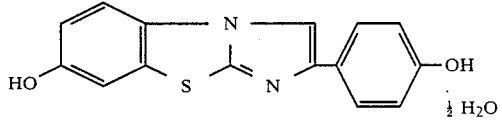

7-Hydroxy-2-(p-hydroxyphenyl)imidazo[2,1-b]benzothiazole hemihydrate melting point above 300° C.
Elemental analysis for $C_{15}H_{10}N_2O_2S\cdot\frac{1}{2}H_2O$:

|  | S (%) |
| --- | --- |
| Calculated: | 11.00 |
| Found: | 11.27 |

EXAMPLE 25

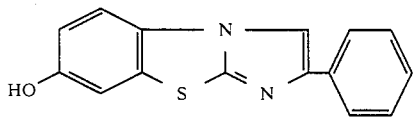

7-Hydroxy-2-phenylimidazo[2,1-b]benzo-
thiazole melting point 234–236° C.
Elemental analysis for $C_{15}H_{10}N_2OS$:

|  | C (%) | H (%) | N (%) | S (%) |
|---|---|---|---|---|
| Calculated: | 67.65 | 3.78 | 10.52 | 12.04 |
| Found: | 67.76 | 3.73 | 10.66 | 11.96 |

EXAMPLE 26

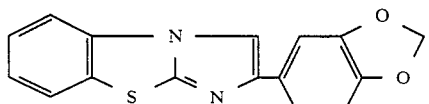

2-(3,4-Methylenedioxyphenyl)imidazo-
[2,1-b]benzothiazole melting point 210–212° C.
Elemental analysis for $C_{16}H_{10}N_2O_2S$:

|  | C (%) | H (%) | N (%) | S (%) |
|---|---|---|---|---|
| Calculated: | 65.29 | 3.42 | 9.52 | 10.89 |
| Found: | 65.34 | 3.35 | 9.55 | 10.74 |

EXAMPLE 27

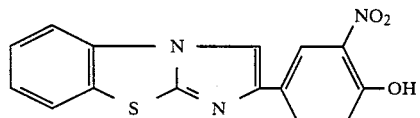

2-(4-Hydroxy-3-nitrophenyl)imidazo[2,1-
b]benzothiazole melting point 264–266° C.
Elemental analysis for $C_{15}H_9N_3O_3S$:

|  | C (%) | H (%) | N (%) |
|---|---|---|---|
| Calculated: | 57.87 | 2.91 | 13.50 |
| Found: | 57.81 | 2.94 | 13.27 |

EXAMPLE 28

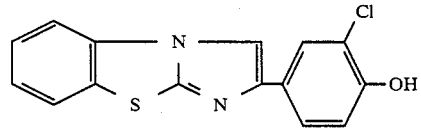

2-(3-Chloro-4-hydroxyphenyl)imidazo-
[2,1-b]benzothiazole melting point 267–269° C.
Elemental analysis for $C_{15}H_9N_2OSCl$:

|  | C (%) | H (%) | N (%) | S (%) |
|---|---|---|---|---|
| Calculated: | 59.90 | 3.02 | 9.31 | 10.66 |
| Found: | 59.76 | 3.12 | 9.22 | 10.78 |

EXAMPLE 29

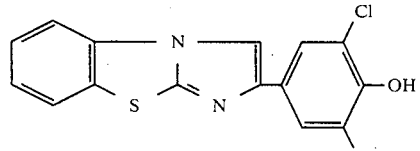

2-(3,5-Dichloro-4-hydroxyphenyl)imi-
dazo[2,1-b]benzothiazole melting point above 310° C.
Elemental analysis for $C_{15}H_8N_2OSCl_2$:

|  | C (%) | H (%) | N (%) |
|---|---|---|---|
| Calculated: | 53.75 | 2.41 | 8.36 |
| Found: | 53.62 | 2.41 | 8.16 |

EXAMPLE 30

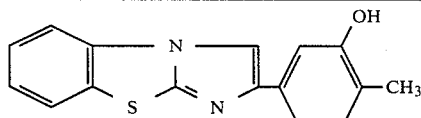

2-(3-Hydroxy-4-methylphenyl)imidazo-
[2,1-b]benzothiazole melting point 308–310° C.
Elemental analysis for $C_{16}H_{12}N_2OS$:

|  | C (%) | H (%) | N (%) | S (%) |
|---|---|---|---|---|
| Calculated: | 68.55 | 4.31 | 9.99 | 11.44 |
| Found: | 68.34 | 4.37 | 9.97 | 11.62 |

EXAMPLE 31

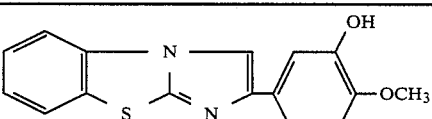

2-(3-Hydroxy-4-methoxyphenyl)imi-
dazo[2,1-b]benzothiazole melting point 160–162° C.
Elemental analysis for $C_{16}H_{12}N_2O_2S$:

|  | C (%) | H (%) | N (%) | S (%) |
|---|---|---|---|---|
| Calculated: | 64.85 | 4.08 | 9.45 | 10.82 |
| Found: | 64.81 | 4.28 | 9.32 | 10.94 |

EXAMPLE 32

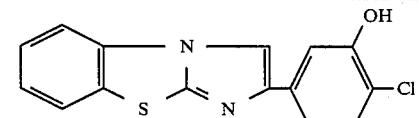

2-(4-chloro-3-hydroxyphenyl)imidazo-
[2,1-b]benzothiazole melting point 310–312° C. (decomposed)
Elemental analysis for $C_{15}H_9N_2OSCl$:

|  | C (%) | H (%) | N (%) | S (%) |
|---|---|---|---|---|
| Calculated: | 59.90 | 3.02 | 9.31 | 10.66 |

-continued

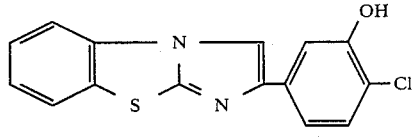

2-(4-chloro-3-hydroxyphenyl)imidazo-
[2,1-b]benzothiazole melting point 310–312° C. (decomposed)
Elemental analysis for $C_{15}H_9N_2OSCl$:

|  | C (%) | H (%) | N (%) | S (%) |
| --- | --- | --- | --- | --- |
| Found: | 59.74 | 2.98 | 9.51 | 10.58 |

EXAMPLE 33

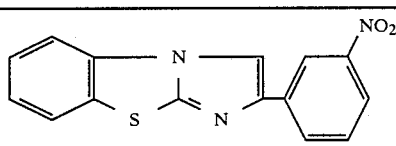

2-(m-Nitrophenyl)imidazo[2,1-b]benzo-
thiazole melting point 232° C.
Elemental analysis for $C_{15}H_9N_3O_2S$:

|  | C (%) | H (%) | N (%) | S (%) |
| --- | --- | --- | --- | --- |
| Calculated: | 61.01 | 3.07 | 14.23 | 10.86 |
| Found: | 60.72 | 2.95 | 14.40 | 10.99 |

EXAMPLE 34

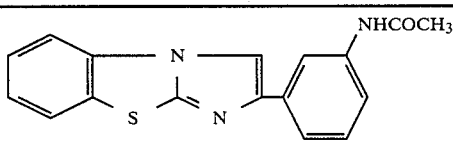

2-(m-Acetamidophenyl)imidazo[2,1-b]-
benzothiazole melting point 232° C.
Elemental analysis for $C_{17}H_{13}N_3OS$:

|  | C (%) | H (%) | N (%) | S (%) |
| --- | --- | --- | --- | --- |
| Calculated: | 66.43 | 4.26 | 13.67 | 10.43 |
| Found: | 66.28 | 4.18 | 13.80 | 10.20 |

EXAMPLE 35

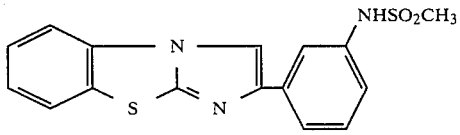

2-(m-Methylsulfonylamidophenyl)imi-
dazo[2,1-b]benzothiazole melting point 194° C.
Elemental analysis for $C_{16}H_{13}N_3O_2S_2$:

|  | C (%) | H (%) | N (%) | S (%) |
| --- | --- | --- | --- | --- |
| Calculated: | 55.96 | 3.82 | 12.24 | 18.68 |
| Found: | 55.67 | 3.90 | 12.39 | 18.94 |

EXAMPLE 36

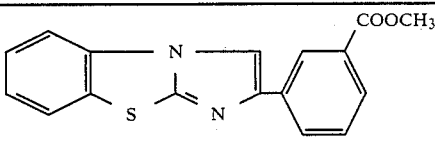

2-(m-Methoxycarbonylphenyl)imidazo-
[2,1-b]benzothiazole melting point 146° C.
Elemental analysis for $C_{17}H_{12}N_2O_2S$:

|  | C (%) | H (%) | N (%) | S (%) |
| --- | --- | --- | --- | --- |
| Calculated: | 66.22 | 3.92 | 9.08 | 10.40 |
| Found: | 66.19 | 3.78 | 9.13 | 10.26 |

EXAMPLE 37

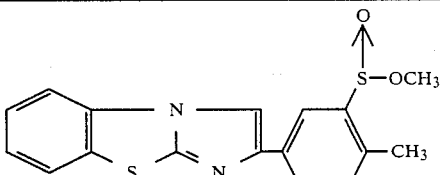

2-(3-Methoxysulfinyl-4-methylphenyl)-
imidazo[2,1-b]benzothiazole melting point 262–264° C.
Elemental analysis for $C_{17}H_{14}N_2O_2S_2$:

|  | C (%) | H (%) | N (%) | S (%) |
| --- | --- | --- | --- | --- |
| Calculated: | 59.63 | 4.12 | 8.18 | 18.73 |
| Found: | 59.46 | 3.98 | 8.31 | 18.43 |

EXAMPLE 38

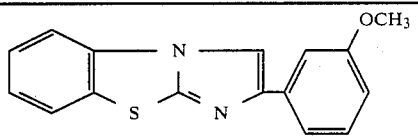

2-(m-Methoxyphenyl)imidazo[2,1-b]benzothiazole melting point 154–156° C.
Elemental analysis for $C_{16}H_{12}N_2OS$:

|  | C (%) | H (%) | N (%) | S (%) |
| --- | --- | --- | --- | --- |
| Calculated: | 68.55 | 4.31 | 9.99 | 11.44 |
| Found: | 68.42 | 4.28 | 10.19 | 11.26 |

EXAMPLE 39

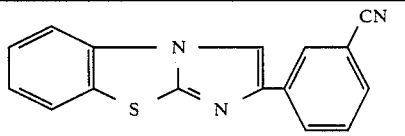

2-(m-cyanophenyl)imidazo[2,1-b]benzothiazole melting point 234° C.
Elemental analysis for $C_{16}H_9N_3S$:

|  | C (%) | H (%) | N (%) | S (%) |
| --- | --- | --- | --- | --- |
| Calculated: | 69.80 | 3.29 | 15.26 | 11.64 |
| Found: | 69.78 | 3.27 | 15.18 | 11.63 |

EXAMPLE 40

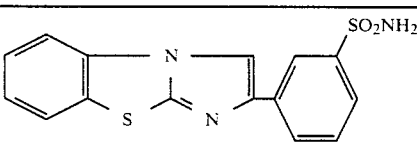

2-(m-sulfamoylphenyl)imidazo[2,1-b]benzothiazole melting point 306° C.
Elemental analysis for $C_{15}H_{11}N_3O_2S_2$:

|  | C (%) | H (%) | N (%) | S (%) |
|---|---|---|---|---|
| Calculated: | 54.70 | 3.37 | 12.76 | 19.47 |
| Found: | 54.54 | 3.51 | 12.44 | 19.32 |

EXAMPLE 41

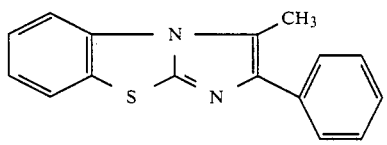

To 50 ml of acetonitrile were added 10 g of 2-aminobenzothiazole and 7 g of α-bromopropiophenone and the mixture was refluxed for 3 days. After cooling the reaction mixture, the precipitated hydrobromide of 2-aminobenzothiazole was filtered off and the filtrate was concentrated under reduced pressure. The residue was dissolved in 50 ml of chloroform and then 100 ml of ethyl acetate was added to the solution. The supernatant formed was recovered and concentrated under reduced pressure. The residue obtained was subjected to silica gel column chromatography and then the product was eluted using chloroform as the eluant to provide 1.5 g of 3-methyl-2-phenylimidazo[2,1-b]benzothiazole.

Melting point: 136–137° C.
Elemental analysis for $C_{16}H_{12}N_2S$:

|  | C (%) | H (%) | N (%) | S (%) |
|---|---|---|---|---|
| Calculated: | 72.70 | 4.58 | 10.60 | 12.13 |
| Found: | 72.50 | 4.54 | 10.47 | 12.20 |

By following the above procedure, the following compounds were prepared.

EXAMPLE 42

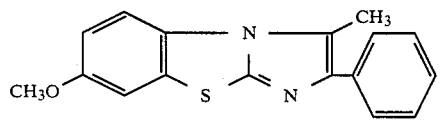

7-Methoxy-3-methyl-2-phenylimidazo[2,1-b]benzothiazole melting point 82–84° C.
Elemental analysis for $C_{17}H_{14}N_2OS$:

|  | C (%) | H (%) | N (%) | S (%) |
|---|---|---|---|---|
| Calculated: | 69.36 | 4.79 | 9.52 | 10.89 |
| Found: | 69.00 | 4.61 | 9.34 | 10.59 |

EXAMPLE 43

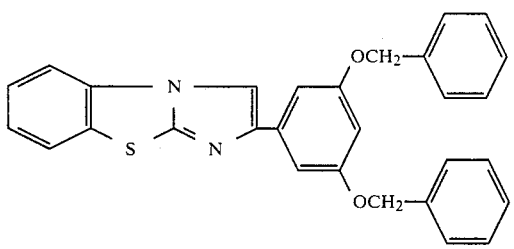

2-(3,5-Dibenzyloxyphenyl)imidazo[2,1-b]benzothiazole melting point 160–161° C.
Elemental analysis for $C_{29}H_{22}N_2O_2S$:

|  | C (%) | H (%) | N (%) | S (%) |
|---|---|---|---|---|
| Calculated: | 75.30 | 4.79 | 6.06 | 6.93 |
| Found: | 75.41 | 4.73 | 5.87 | 7.08 |

EXAMPLE 44

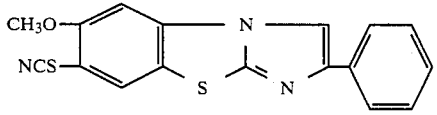

6-Methoxy-2-phenyl-7-thiocyanatoimidazo[2,1-b]benzothiazole melting point 217–220° C.
Elemental analysis for $C_{17}H_{11}N_3S_2O$:

|  | C (%) | H (%) | N (%) |
|---|---|---|---|
| Calculated: | 60.52 | 3.29 | 12.45 |
| Found: | 60.38 | 3.22 | 12.26 |

EXAMPLE 45

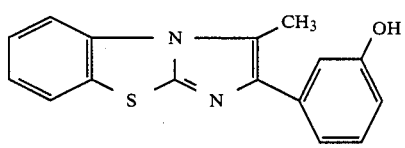

2-(m-Hydroxyphenyl)-3-methylimidazo[2,1-b]benzothiazole melting point 246–248° C.
Elemental analysis for $C_{16}H_{12}N_2OS$:

|  | N (%) |
|---|---|
| Calculated: | 9.99 |
| Found: | 9.78 |

EXAMPLE 46

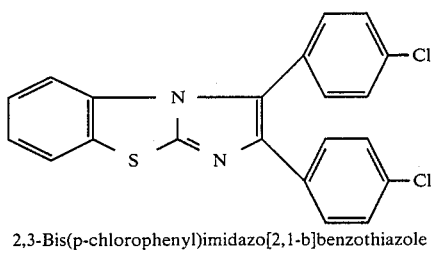

2,3-Bis(p-chlorophenyl)imidazo[2,1-b]benzothiazole melting point 235° C.
Elemental analysis for $C_{21}H_{12}N_2SCl_2$:

|  | C (%) | H (%) | N (%) | S (%) |
| --- | --- | --- | --- | --- |
| Calculated: | 63.81 | 3.06 | 7.09 | 8.11 |
| Found: | 64.01 | 3.00 | 7.11 | 8.10 |

EXAMPLE 47

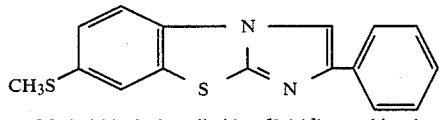

7-Methylthio-2-phenylimidazo[2,1-b]benzothiazole melting point 149° C.
Elemental analysis for $C_{16}H_{12}N_2S_2$:

|  | C (%) | H (%) | N (%) | S (%) |
| --- | --- | --- | --- | --- |
| Calculated: | 64.84 | 4.08 | 9.45 | 21.63 |
| Found: | 64.59 | 3.98 | 9.34 | 21.59 |

EXAMPLE 48

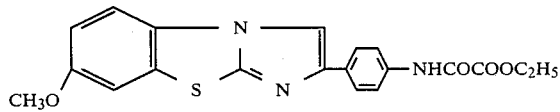

By following the same procedure as in Example 1 using 3.6 g of 2-amino-6-methoxybenzothiazole and 6 g of p-ethoxalylamidophenacyl bromide as starting materials, 5.3 g of the white crystals of 2-imino-3-(p-ethoxalylamidobenzoylmethyl)-6-methoxy-2,3-dihydrobenzothiazole hydrobromide were obtained. The white crystals were refluxed in 150 ml of methylcellosolve for 3 hours. After cooling the reaction mixture, crystals formed were recovered by filtration and the filtrate was concentrated under reduced pressure to form a solid material. The crystals recovered above were combined with the solid material and after adding thereto 30 ml of saturated sodium hydrogencarbonate solution, the product was extracted with 300 ml of chloroform. The chloroform extract was dried with anhydrous magnesium sulfate and concentrated under reduced pressure to provide 2.5 g of 2-(p-ethoxalylamidophenyl)-7-methoxyimidazo[2,1-b]benzothiazole.

Melting point: 218–219° C.
Elemental analysis for $C_{20}H_{17}N_3O_4S$:

|  | C (%) | H (%) | N (%) | S (%) |
| --- | --- | --- | --- | --- |
| Calculated: | 60.75 | 4.33 | 10.63 | 8.11 |
| Found: | 60.61 | 4.27 | 10.45 | 8.03 |

EXAMPLE 49

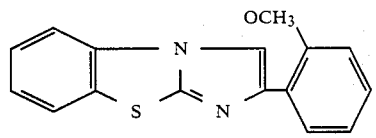

To 70 ml of methyl ethyl ketone were added 7 g of 2-aminobenzothiazole and 10 g of o-methoxyphenacyl bromide and the mixture was refluxed for 10 hours. The reaction mixture was filtered while it was hot to recover crystals precipitated. The crystals were washed with methyl ethyl ketone, and dried to provide 3.0 g of 2-(o-methoxyphenyl)imidazo[2,1-b]-benzothiazole hydrobromide having a melting point of 263°–265° C.

Then, 3 g of the hydrobromide was added to a mixture of 50 ml of chloroform and 20 ml of 20% aqueous ammonia and after stirring the mixture for 20 minutes at room temperature, the chloroform layer formed was recovered. The chloroform layer obtained was washed with water, dried with anhydrous magnesium sulfate, and concentrated under reduced pressure to form white solid materials, which were recrystallized from toluene-n-hexane to provide 1.9 g of 2-(o-methoxyphenyl)imidazo[2,1-b]-benzothiazole.

Melting point: 183–185° C.
Elemental analysis for $C_{16}H_{12}N_2OS$:

|  | C (%) | H (%) | N (%) | S (%) |
| --- | --- | --- | --- | --- |
| Calculated: | 68.55 | 4.31 | 9.99 | 11.44 |
| Found: | 68.65 | 4.26 | 9.95 | 11.32 |

EXAMPLE 50

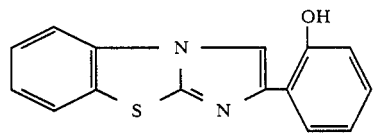

To 50 ml of methyl ethyl ketone were added 7.5 g of 2-aminobenzothiazole and 12 g of o-acetoxyphenacyl bromide and the mixture was refluxed for 3 hours. After the reaction was over, the reaction mixture was cooled, the hydrobromide of 2-aminobenzothiazole precipitated was filtered away and the filtrate was concentrated under reduced pressure and then toluene was added to the residue, thereby crystals precipitated. The crystals were recovered by filtration and dried to provide 3.5 g of the white crystals of 2-imino-3-(o-hydroxybenzoylmethyl)-2,3-dihydrobenzothiazole.

Then, 2.2 g of the crystals were treated with alcoholic hydrochloric acid to form the hydrochloride, which was heated together with 50 ml of methylcellosolve and treated as in Example 1 to provide 1.6 g of the white crystals of 2-(o-hydroxyphenyl)imidazo[2,1-b]benzothiazole.

| Melting point: 191–192° C. | | | | |
|---|---|---|---|---|
| Elemental analysis for C$_{15}$H$_{10}$N$_2$OS: | | | | |
|  | C (%) | H (%) | N (%) | S (%) |
| Calculated: | 67.65 | 3.78 | 10.52 | 12.04 |
| Found: | 67.51 | 3.79 | 10.40 | 11.73 |

EXAMPLE 51

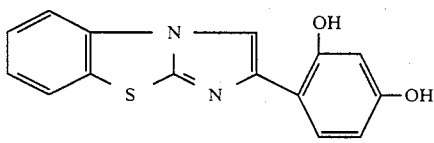

A solution of 6.8 g of 2-aminobenzothiazole and 7.2 g of 2,4-diacetoxy-α-bromoacetophenone in 100 ml of methyl ethyl ketone was refluxed for 3 hours. After cooling the reaction mixture, 50 ml of ether was added to the reaction mixture, the precipitates formed were filtered away, and the mother liquor was concentrated under reduced pressure. The residue formed was dissolved in 10 ml of tetrahydrofuran and 10 ml of ether and then the solution was acidified by the addition of a hydrogen chloride-ethanol solution. Crystals formed which were recovered by filtration, dried and then refluxed together with 50 ml of methylcellosolve for 5 hours. The reaction mixture was alkalified by the addition of concentrated aqueous ammonia and then cooled to form crystals, which were recovered by filtration and recrystallized from tetrahydrofuran-n-hexane to provide 1 g of 2-(2,4-dihydroxyphenyl)imidazo[2,1-b]benzothiazole.

| Melting point: 254–257° C. | | | |
|---|---|---|---|
| Elemental analysis for C$_{15}$H$_{10}$N$_2$O$_2$S | | | |
|  | C (%) | H (%) | N (%) |
| Calculated: | 63.82 | 3.57 | 9.92 |
| Found: | 63.62 | 3.53 | 9.77 |

EXAMPLE 52

By following the above procedure, following compound was prepared.

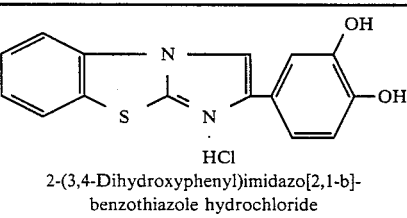

HCl
2-(3,4-Dihydroxyphenyl)imidazo[2,1-b]-
benzothiazole hydrochloride

| melting point 235° C. | | |
|---|---|---|
| Elemental analysis for C$_{15}$H$_{11}$N$_2$O$_2$SCl: | | |
|  | S (%) | Cl (%) |
| Calculated: | 10.06 | 11.12 |
| Found: | 9.76 | 11.18 |

EXAMPLE 53

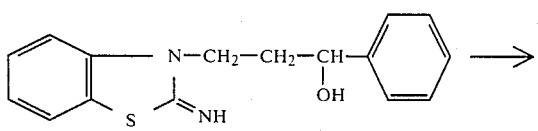

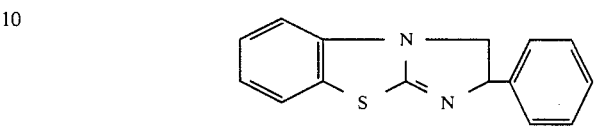

After refluxing 4 g of 2-imino-3-(β-hydroxyphenetyl)-2,3-dihydrobenzothiazole hydrochloride together with 40 ml of chloroform and 9 ml of thionyl chloride for 2 hours, the reaction mixture was concentrated under reduced pressure to provide 4.2 g of the crude crystals of 2-imino-3-(β-chlorophenethyl)-2,3-dihydrobenzothiazole hydrochloride. To the product were added 50 ml of chloroform, 50 ml of water, and 5 g of sodium hydrogencarbonate and the mixture was refluxed for 3 hours. After the reaction was over, the chloroform layer was washed with water, dried with anhydrous magnesium sulfate, and concentrated under reduced pressure to provide a tacky material. The tacky product was treated with hydrochloric acid-ethanol and the white solid materials thus obtained were recrystallized from ethanol to provide 1.4 g of 2-phenyl-2,3-dihydroimidazo[2,1-b]benzothiazole hydrochloride.

| Nuclear magnetic resonance spectra (D$_6$—DMSO) | | | |
|---|---|---|---|
| δ(ppm): | 4.39 | 5.03 | (2H, —CH$_2$—) |
|  | 6.01 |  | (1H, —CH—) |
|  | 7.2–8.2 |  | (9H, H of aromatic ring) |

In addition, 2-amino-3-(β-hydroxyphenetyl)-2,3-dihydrobenzothiazole hydrochloride used above as the starting material was prepared as follows:

In 100 ml of ethanol was suspended 7.5 g of 2-imino-3-phenacyl-2,3-dihydrobenzothiazole hydrobromide and after cooling the suspension to 0° C. to 5° C., 1.2 g of sodium borohydride was gradually added to the suspension, and the mixture was stirred for one hour. The reaction mixture was mixed with 5 ml of water and concentrated under reduced pressure. The residue was extracted with toluene and the extract was washed with water, dried with anhydrous magnesium sulfate, and then the solvent was distilled off to provide a tacky residue. The tacky product was dissolved in ethanol and hydrochloric acid-ethanol was added to the solution to provide 6 g of 2-imino-3-(β-hydroxyphenethyl)-2,3-dihydrobenzothiazole hydrochloride. Melting point: 253°–255° C.

EXAMPLE 54

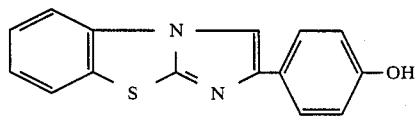

In a solution of 2.5 g of potassium hydroxide in 90% methanol was suspended 2 g of 2-(p-acetoxyphenyl)imidazo-[2,1-b]benzothiazole and the suspension was stirred for one hour at 40°–50° C., thereby the additive was completely dissolved. Then, 3 ml of acetic acid was gradually added dropwise to the reaction mixture with stirring, thereby crystals precipitated. The crystals were recovered by filtration, washed with water and then methanol, and dried to provide 1.5 g of 2-(p-hydroxyphenyl)imidazo[2,1-b]benzothiazole.

| Melting point: 296–298° C. Elemental analysis for $C_{15}H_{10}N_2OS$: | | | | |
|---|---|---|---|---|
| | C | H | N | S |
| Calculated: | 67.65% | 3.78% | 10.52% | 12.04% |
| Found: | 67.48% | 3.77% | 10.39% | 12.07% |

By following the above procedure, the following compounds were prepared.

EXAMPLE 55

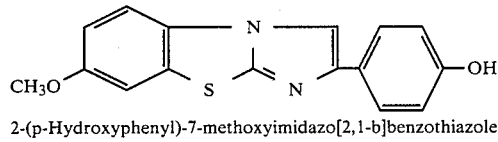

2-(p-Hydroxyphenyl)-7-methoxyimidazo[2,1-b]benzothiazole

| melting point 285–286° C. Elemental analysis for $C_{16}H_{12}N_2O_2S$: | | | | |
|---|---|---|---|---|
| | C (%) | H (%) | N (%) | S (%) |
| Calculated: | 64.85 | 4.08 | 9.45 | 10.82 |
| Found: | 64.64 | 3.98 | 9.49 | 10.99 |

EXAMPLE 56

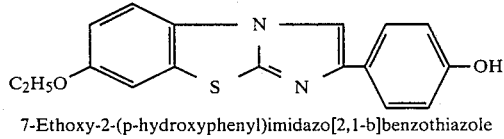

7-Ethoxy-2-(p-hydroxyphenyl)imidazo[2,1-b]benzothiazole

| melting point 261–263° C. Elemental analysis for $C_{17}H_{14}N_2O_2S$: | | | | |
|---|---|---|---|---|
| | C (%) | H (%) | N (%) | S (%) |
| Calculated: | 65.79 | 4.55 | 9.03 | 10.33 |
| Found: | 65.51 | 4.73 | 8.78 | 10.20 |

EXAMPLE 57

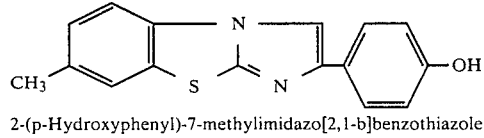

2-(p-Hydroxyphenyl)-7-methylimidazo[2,1-b]benzothiazole

| melting point 279–282° C. Elemental analysis for $C_{16}H_{12}N_2OS$: | | | | |
|---|---|---|---|---|
| | C (%) | H (%) | N (%) | S (%) |
| Calculated: | 68.55 | 4.31 | 9.99 | 11.44 |
| Found: | 68.25 | 4.20 | 9.82 | 11.57 |

EXAMPLE 58

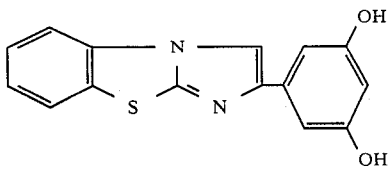

2-(3,5-Dihydroxyphenyl)imidazo[2,1-b]benzothiazole

| melting point 287–290° C. (decomposed) Elemental analysis for $C_{15}H_{10}N_2O_2S$: | | | | |
|---|---|---|---|---|
| | C (%) | H (%) | N (%) | S (%) |
| Calculated: | 63.82 | 3.57 | 9.92 | 11.36 |
| Found: | 63.54 | 3.72 | 9.71 | 11.20 |

EXAMPLE 59

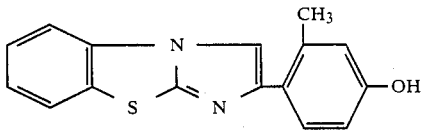

2-(4-Hydroxy-2-methylphenyl)imidazo[2,1-b]benzothiazole

| melting point 253–255° C. Elemental analysis for $C_{16}H_{12}N_2OS$: | | | | |
|---|---|---|---|---|
| | C (%) | H (%) | N (%) | S (%) |
| Calculated: | 68.55 | 4.31 | 9.99 | 11.44 |
| Found: | 68.50 | 4.21 | 10.16 | 11.31 |

EXAMPLE 60

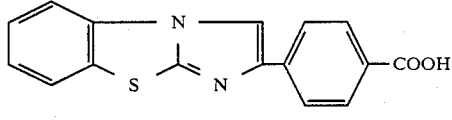

To a mixture of 15 ml of an aqueous solution of 20% potassium hydroxide and 50 ml of methanol was added 2.2 g of 2-(p-methoxycarbonylphenyl)imidazo[2,1-b]benzothiazole and the mixture was refluxed for 30 minutes. After the reaction was over, 4 ml of acetic acid was added to the reaction mixture and the crystals which had formed were recovered by filtration, washed successively with water, methanol and then ethanol, and dried to provide 1.7 g of 2-(p-carboxyphenyl)imidazo[2,1-b]benzothiazole.

| Melting point: above 300° C. Elemental analysis for $C_{16}H_{10}N_2O_2S$: | | | | |
|---|---|---|---|---|
| | C (%) | H (%) | N (%) | S (%) |
| Calculated: | 65.29 | 3.42 | 9.52 | 10.89 |
| Found: | 65.24 | 3.34 | 9.33 | 11.07 |

By following the above procedure, the following compounds were prepared.

EXAMPLE 61

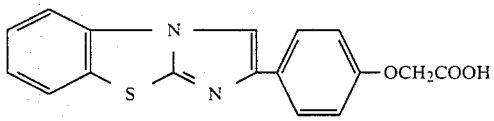

2-[p-(Carboxymethoxy)phenyl]imidazo[2,1-b]benzothiazole
melting point 255° C.
Elemental analysis for $C_{17}H_{12}N_2O_3S$:

|  | C (%) | H (%) | N (%) | S (%) |
|---|---|---|---|---|
| Calculated: | 62.95 | 3.73 | 8.64 | 9.88 |
| Found: | 62.65 | 3.84 | 8.59 | 9.66 |

EXAMPLE 62

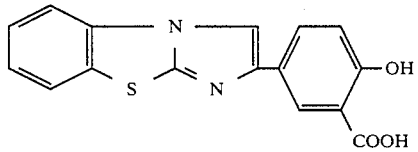

2-(3-Carboxy-4-hydroxyphenyl)imidazo[2,1-b]benzothiazole
melting point above 300° C.
Elemental analysis for $C_{16}H_{10}N_2O_3S$:

|  | C (%) | H (%) | N (%) | S (%) |
|---|---|---|---|---|
| Calculated: | 61.93 | 3.25 | 9.03 | 10.33 |
| Found: | 61.81 | 3.19 | 9.11 | 10.61 |

EXAMPLE 63

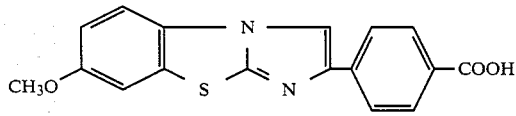

2-(p-Carboxyphenyl)-7-methoxyimidazo[2,1-b]benzothiazole
melting point above 300° C.
Elemental analysis for $C_{17}H_{12}N_2O_3S$:

|  | C (%) | H (%) | N (%) | S (%) |
|---|---|---|---|---|
| Calculated: | 62.95 | 3.73 | 8.64 | 9.88 |
| Found: | 62.71 | 3.57 | 8.80 | 10.25 |

EXAMPLE 64

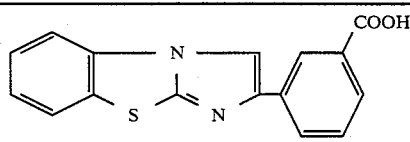

2-(m-Carboxyphenyl)imidazo[2,1-b]benzothiazole
melting point above 300° C.
Elemental analysis for $C_{16}H_{10}N_2O_2S$:

|  | C (%) | H (%) | N (%) | S (%) |
|---|---|---|---|---|
| Calculated: | 65.29 | 3.42 | 9.52 | 10.68 |
| Found: | 65.32 | 3.39 | 9.51 | 10.94 |

EXAMPLE 65

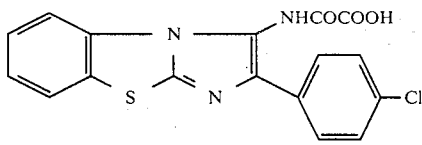

In 600 ml of water was suspended 2.08 g of 2-(p-chlorophenyl)-3-ethoxalylamidoimidazo[2,1-b]benzothiazole and then after adding 10 ml of a 1 normal sodium hydroxide solution to the suspension, the mixture was stirred for 3 hours at room temperature. Insoluble materials were filtered away and acetic acid was added to the filtrate to form crystals, which were recovered by filtration, washed with water, and dried to provide 1.1 g of 2-(p-chlorophenyl)-3-oxaloamidoimidazo[2,1-b]benzothiazole.

Mass spectrum m/e: 271 (M$^+$)
Elemental analysis for $C_{17}H_{10}N_3O_3SCl$)

|  | S (%) |
|---|---|
| Calculated: | 8.62 |
| Found: | 8.68 |

EXAMPLE 66

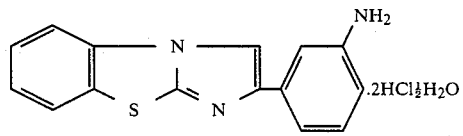

To a mixture of 30 ml of a 2 normal hydrochloric acid solution and 20 ml of methanol was added 4 g of 2-(m-acetamidophenyl)imidazo[2,1-b]benzothiazole and the mixture was refluxed for 2 hours. The reaction mixture was concentrated under reduced pressure to form solid materials, which were recrystallized from ethanol to provide 4.2 g of 2-(m-aminophenyl)imidazo[2,1-b]benzothiazole di-hydrochloride hemihydrate.

Melting point: 241° C.
Elemental analysis for $C_{15}H_{13}N_3SCl_2.\frac{1}{2}H_2O$)

|  | C (%) | H (%) | N (%) | S (%) | Cl (%) |
|---|---|---|---|---|---|
| Calculated: | 51.88 | 4.06 | 12.10 | 9.23 | 20.42 |
| Found: | 52.13 | 3.94 | 12.04 | 9.19 | 20.15 |

EXAMPLE 67

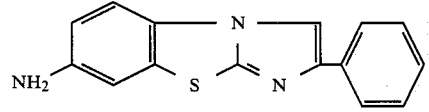

To a mixture of 100 ml of concentrated hydrochloric acid solution and 300 ml of methylcellosolve was added 8.5 g of 7-acetamido-2-phenylimidazo[2,1-b]benzothiazole mono-hydrate and the mixture was stirred for 4 hours at 100°-110° C. The reaction mixture was cooled to form crystals, which were recovered by filtration. The crystals were suspended in 200 ml of methylcellosolve and after alkalifying the suspension by adding concentrated aqueous ammonia, 80 ml of water was added to the mixture followed by cooling, thereby crystals precipitated. The crystals precipitated were recovered by filtration and dried to provide 5.76 g of 7-amino-2-phenylimidazo[2,1-b]benzothiazole.

| Melting point: 161–163° C. Elemental analysis for $C_{15}H_{11}N_3S$: | | | | |
|---|---|---|---|---|
| | C (%) | H (%) | N (%) | S (%) |
| Calculated: | 67.90 | 4.18 | 15.84 | 12.08 |
| Found: | 67.99 | 4.11 | 15.80 | 12.12 |

EXAMPLE 68

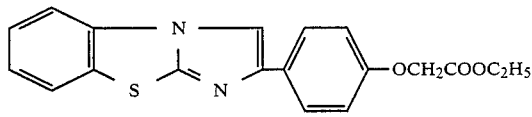

To 40 ml of methyl ethyl ketone were added 2.6 g of 2-(p-hydroxyphenyl)imidazo[2,1-b]benzothiazole, 1.7 g of monobromoacetic acid ethyl ester, and 1.5 g of potassium carbonate and the mixture was refluxed overnight. After the reaction was over, the reaction mixture was cooled, insoluble materials were filtered off, and the filtrate was concentrated under reduced pressure to provide solid materials, which were recrystallized from toluene-n-hexane to provide 1.8 g of 2-(p-ethoxycarbonylmethoxyphenyl)imidazo[2,1-b]benzothiazole.

| Melting point: 129–130° C. Elemental analysis for $C_{19}H_{16}N_2O_3S$: | | | | |
|---|---|---|---|---|
| | C (%) | H (%) | N (%) | S (%) |
| Calculated: | 64.76 | 4.58 | 7.95 | 9.10 |
| Found: | 64.58 | 4.51 | 7.73 | 8.80 |

By following the above procedure, the following compound was prepared.

EXAMPLE 69

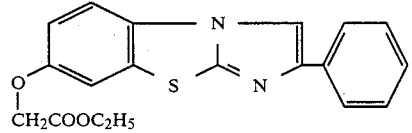

7-Ethoxycarbonylmethoxy-2-phenylimidazo[2,1-b]benzothiazole melting point 114–116° C.

| Elemental analysis for $C_{19}H_{16}N_2O_3S$: | | | | |
|---|---|---|---|---|
| | C (%) | H (%) | N (%) | S (%) |
| Calculated: | 64.76 | 4.58 | 7.95 | 9.10 |
| Found: | 64.61 | 4.56 | 7.89 | 9.15 |

EXAMPLE 70

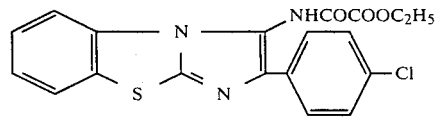

In a mixture of 15 ml of pyridine and 15 ml of methylene chloride was dissolved 1.8 g of 3-amino-2-(p-chlorophenyl)imidazo[2,1-b]benzothiazole and then a solution of 1.5 g of ethyloxalyl chloride in 10 ml of methylene chloride was added dropwise to the solution at temperatures below 5° C. The temperature of the mixture was allowed to raise to room temperature and after stirring the mixture for 3 hours, the reaction mixture was concentrated under reduced pressure. The residue was extracted with 400 ml of ethyl acetate and the extract was washed with water, dried with anhydrous magnesium sulfate, and concentrated under reduced pressure to form crystals, which were recovered and recrystallized from ethanol to provide 1.72 g of 2-(p-chlorophenyl)-3-ethoxalylamino-imidazo[2,1-b]benzothiazole.

| Melting point: 243–245° C. Elemental analysis for $C_{19}H_{14}O_3N_3SCl$: | | | |
|---|---|---|---|
| | C | H | N |
| Calculated: | 57.07 | 3.53 | 10.51 |
| Found: | 57.05 | 3.47 | 10.35 |

By following the above procedure, the compound shown in the following example was prepared.

EXAMPLE 71

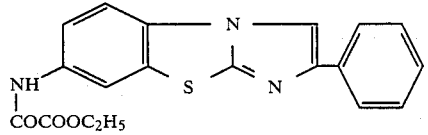

7-Ethoxalylamido-2-phenylimidazo[2,1-b]benzothiazole melting point 238–241° C.

| Elemental analysis for $C_{19}H_{15}N_3O_3S$: | | | | |
|---|---|---|---|---|
| | C (%) | H (%) | N (%) | S (%) |
| Calculated: | 62.45 | 4.14 | 11.50 | 8.77 |
| Found: | 62.20 | 4.07 | 11.43 | 9.07 |

EXAMPLE 72

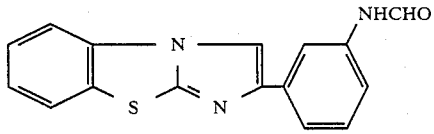

To 15 ml of a mixture of acetic anhydride and formic acid in a 5:3 by volume ratio was added 1.2 g of 2-(m-aminophenyl)-imidazo[2,1-b]benzothiazole under cooling to 3°–10° C. and then the mixture was stirred for one hour at room temperature. To the reaction mixture was added 100 ml of water and then the product was extracted with a mixture of 25 ml of toluene and 25 ml of ethyl acetate. The extract was washed with water and then an aqueous sodium hydrogencarbonate solution, dried with anhydrous magnesium sulfate, and concentrated under reduced pressure to provide 1.2 g of the white crystals of 2-(m-formamidophenyl)imidazo[2,1-b]benzothiazole.

| Melting point: 163° C. Elemental analysis for $C_{16}H_{11}N_3OS$: | | | | |
|---|---|---|---|---|
| | C (%) | H (%) | N (%) | S (%) |
| Calculated: | 65.51 | 3.78 | 14.32 | 10.93 |
| Found: | 65.54 | 3.82 | 14.40 | 11.00 |

EXAMPLE 73

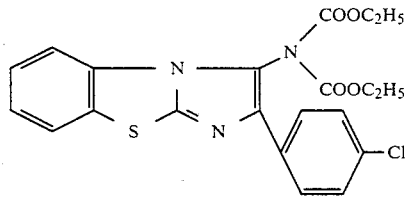

To a solution of 1.5 g of 3-amino-2-(p-chlorophenyl)-imidazo[2,1-b]benzothiazole in 10 ml of pyridine was added dropwise a solution of 1.2 g of ethyl chlorocarbonate in 5 ml of methylene chloride at temperatures below 10° C. Thereafter, the mixture was stirred overnight at room temperature and concentrated under reduced pressure. The residue was extracted with ethyl acetate. The extract was washed with water, dried with anhydrous magnesium sulfate, and concentrated under reduced pressure to form crystals, which were recovered and recrystallized from ethanol to provide 1.56 g of 2-(p-chlorophenyl)-3-bis(ethoxycarbonyl)amidoimidazo[2,1-b]benzothiazole.

| Melting point: 140–142° C. Elemental analysis for $C_{21}H_{18}N_3O_4SCl$: | | | | | |
|---|---|---|---|---|---|
| | C (%) | H (%) | N (%) | S (%) | Cl (%) |
| Calculated: | 56.82 | 4.09 | 9.47 | 7.22 | 7.99 |
| Found: | 56.67 | 4.08 | 9.39 | 7.35 | 8.13 |

EXAMPLE 74

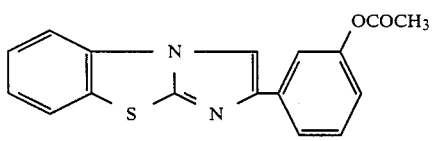

A solution of 2.3 g of 2-(m-hydroxyphenyl)imidazo[2,1-b]benzothiazole in 3 ml of acetic anhydride and 10 ml of pyridine was stirred overnight at 80° C. The reaction mixture was concentrated under reduced pressure and the residue formed was extracted with ethyl acetate. The extract was washed with water, dried by with anhydrous magnesium sulfate, and concentrated under reduced pressure. The residue was subjected to silica gel column chromatography using a 10:3 mixture of toluene and ethyl acetate as an eluant and the crystals obtained were recrystallized from a mixture of toluene and n-hexane to provide 1.35 g of 2-(m-acetoxyphenyl)imidazo[2,1-b]benzothiazole.

| Melting point: 101–102° C. Elemental analysis for $C_{17}H_{12}N_2O_2S$: | | | | |
|---|---|---|---|---|
| | C (%) | H (%) | N (%) | S (%) |
| Calculated: | 66.22 | 3.92 | 9.08 | 10.40 |
| Found: | 66.01 | 3.92 | 8.87 | 10.53 |

EXAMPLE 75

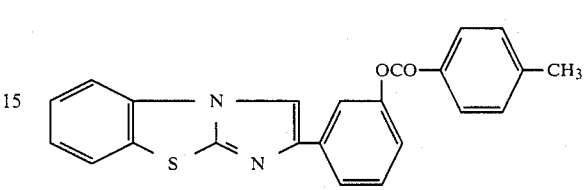

To a solution of 1.5 g of 2-(m-hydroxyphenyl)imidazo[2,1-b]benzothiazole in 100 ml of tetrahydrofuran and 2 ml of triethylamine was added a solution of 0.96 g of p-toluoyl chloride in 10 ml of tetrahydrofuran at temperatures below 10° C. and the mixture was stirred overnight at room temperature. The reaction mixture was mixed with 100 ml of toluene, washed with water, dried with anhydrous magnesium sulfate, and concentrated under reduced pressure. The residue was recrystallized from a mixture of toluene and n-hexane to provide 2 g of 2-[3-(p-toluoyloxy)phenyl]imidazo[2,1-b]benzothiazole.

| Melting point: 173–175° C. Elemental analysis for $C_{23}H_{16}N_2O_2S$: | |
|---|---|
| | S (%) |
| Calculated: | 8.34 |
| Found: | 8.36 |

EXAMPLE 76

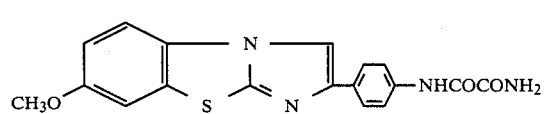

To 2.5 g of 2-(p-ethoxalylamidophenyl)-7-methoxyimidazo[2,1-b]benzothiazole were added 50 ml of methyl cellosolve and 10 ml of 30% aqueous ammonia and after stirring the mixture for one hour at room temperature, the crystals which formed were recovered by filtration, washed successively with chloroform and then methanol and dried to provide 1.9 g of 7-methoxy-2-(p-oxamidophenyl)imidazo[2,1-b]benzothiazole.

| Melting point: above 300° C. Elemental analysis for $C_{18}H_{14}N_4O_3S$: | | | | |
|---|---|---|---|---|
| | C (%) | H (%) | N (%) | S (%) |
| Calculated: | 59.01 | 3.85 | 15.29 | 8.75 |
| Found: | 58.74 | 3.82 | 15.02 | 8.63 |

EXAMPLE 77

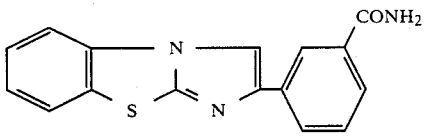

To 50 ml of a methanol solution containing 9 g of ammonia was added 3.2 g of 2-(m-methoxycarbonyl-phenyl)imidazo[2,1-b]benzothiazole and the mixture was stirred overnight in a closed tube at 100°–110° C. After cooling the mixture, crystals precipitated were recovered by filtration, washed with chloroform, and dried to provide 2 g of the white crystals of 2-(m-carbamoylphenyl)imidazo[2,1-b]benzothiazole.

Melting point: 261° C.
Elemental analysis for $C_{16}H_{11}N_3OS$:

|  | C (%) | H (%) | N (%) | S (%) |
|---|---|---|---|---|
| Calculated: | 65.51 | 3.78 | 14.32 | 10.93 |
| Found: | 65.26 | 3.65 | 14.18 | 10.97 |

EXAMPLE 78

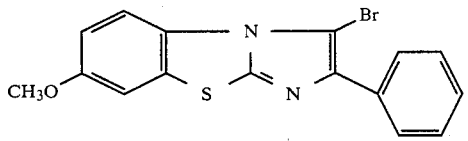

While stirring vigorously a mixture of a solution of 2.0 g of 7-methoxy-2-phenylimidazo[2,1-b]benzothiazole in 50 ml of chloroform and 30 ml of a saturated aqueous sodium hydrogencarbonate solution, a solution of 1.2 g of bromine in 5 ml of chloroform was gradually added dropwise to the mixture at room temperature. Thereafter, the chloroform layer was recovered, dried by anhydrous magnesium sulfate, and concentrated under reduced pressure to form a solid material. The solid product was recrystallized from a mixture of toluene and n-hexane to provide 2.0 g of 3-bromo-7-methoxy-2-phenylimidazo[2,1-b]benzothiazole.

Melting point: 180° C.
Elemental analysis for $C_{16}H_{11}BrN_2OS$:

|  | C (%) | H (%) | N (%) | S (%) | Br (%) |
|---|---|---|---|---|---|
| Calculated: | 53.50 | 3.09 | 7.80 | 8.92 | 22.24 |
| Found: | 53.36 | 2.94 | 7.33 | 9.08 | 22.42 |

By following the above procedure, the following compounds were prepared.

EXAMPLE 79

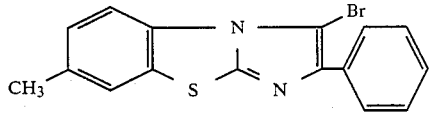

3-Bromo-7-methyl-2-phenylimidazo[2,1-b]benzothiazole
melting point 178–180° C.
Elemental analysis for $C_{16}H_{11}BrN_2S$:

|  | C (%) | H (%) | N (%) | S (%) | Br (%) |
|---|---|---|---|---|---|
| Calculated: | 55.99 | 3.23 | 8.16 | 9.34 | 23.28 |
| Found: | 55.94 | 3.08 | 8.01 | 9.44 | 23.47 |

EXAMPLE 80

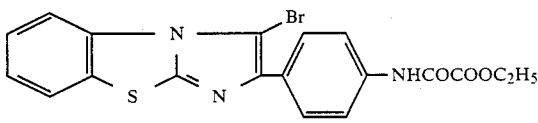

3-Bromo-2-[p-ethoxalylamido)phenyl]imidazo[2,1-b]benzothiazole
melting point 237–238° C.
Elemental analysis for $C_{19}H_{14}O_3N_3SBr$:

|  | C (%) | H (%) | N (%) | S (%) |
|---|---|---|---|---|
| Calculated: | 51.36 | 3.18 | 9.46 | 7.22 |
| Found: | 51.27 | 3.03 | 9.27 | 7.24 |

EXAMPLE 81

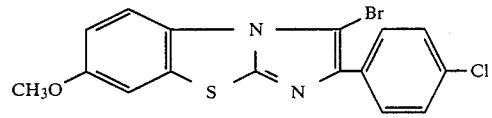

3-Bromo-2-p-chlorophenyl)-7-methoxyimidazo[2,1-b]benzothiazole
melting point 239° C.
Elemental analysis for $C_{16}H_{10}N OSClBr$:

|  | C (%) | H (%) | N (%) | S (%) |
|---|---|---|---|---|
| Calculated: | 48.81 | 2.56 | 7.12 | 8.14 |
| Found: | 48.76 | 2.40 | 7.07 | 8.34 |

EXAMPLE 82

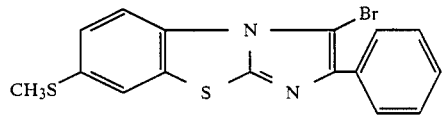

3-Bromo-7-methylthio-2-phenylimidazo[2,1-b]benzothiazole
melting point 144° C.
Elemental analysis for $C_{16}H_{11}N_2S_2Br$:

|  | C (%) | H (%) | N (%) | S (%) |
|---|---|---|---|---|
| Calculated: | 51.21 | 2.95 | 7.46 | 17.08 |
| Found: | 51.37 | 2.91 | 7.71 | 17.27 |

EXAMPLE 83

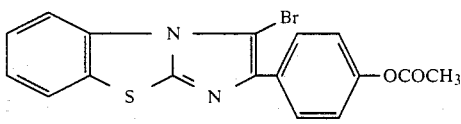

2-(p-Acetoxyphenyl)-3-bromoimidazo[2,1-b]benzothiazole
melting point 210° C.
Elemental analysis for $C_{17}H_{11}N_2O_2SBr$:

|  | C (%) | H (%) | N (%) | S (%) |
|---|---|---|---|---|
| Calculated: | 52.73 | 2.86 | 7.23 | 8.28 |
| Found: | 52.81 | 2.71 | 7.18 | 8.30 |

EXAMPLE 84

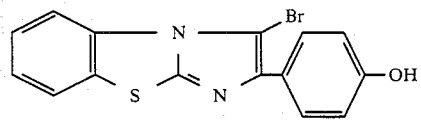

3-Bromo-2-(p-hydroxyphenyl)imidazo[2,1-b]benzothiazole
melting point 219° C.
Elemental analysis for $C_{15}H_9N_2OSBr$:

|  | C (%) | H (%) | N (%) | S (%) | Br (%) |
|---|---|---|---|---|---|
| Calculated: | 52.19 | 2.63 | 8.11 | 9.29 | 23.15 |
| Found: | 52.09 | 2.54 | 7.88 | 9.20 | 23.43 |

EXAMPLE 85

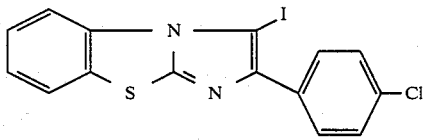

In 100 ml of methylene chloride was dissolved 2 g of 2-(p-chlorophenyl)imidazo[2,1-b]benzothiazole and after adding thereto 20 ml of an aqueous 10% potassium hydrogencarbonate solution and 1.8 g of iodine, the mixture was stirred overnight vigorously at room temperature. The crystals which formed were recovered by filtration and recrystallized from a mixture of methylcellosolve and water to provide 2.4 g of 2-(p-chlorophenyl)-3-iodoimidazo[2,1-b]benzothiazole.

Melting point: 253-255° C.
Elemental analysis for $C_{15}H_8N_2SCl I$:

|  | C (%) | H (%) | N (%) | S (%) |
|---|---|---|---|---|
| Calculated: | 43.87 | 1.96 | 6.82 | 7.81 |
| Found: | 43.90 | 1.80 | 6.78 | 8.08 |

EXAMPLE 86

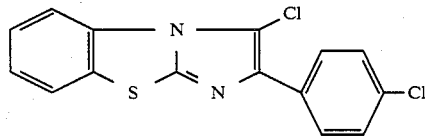

To a solution of 2 g of 2-(p-chlorophenyl)imidazo[2,1-b]benzothiazole in 40 ml of methylene chloride was added a solution of 0.95 g of sulfuryl chloride in 5 ml of methylene chloride and after stirring for 10 minutes, 40 ml of an aqueous 10% potassium hydrogencarbonate solution was added to the mixture followed by stirring. The organic layer which formed was recovered, washed with water, dried with anhydrous magnesium sulfate, and concentrated under reduced pressure to form crystals, which were recrystallized from ethanol to provide 1.4 g of 3-chloro-2-(p-chlorophenyl)imidazo[2,1-b]benzothiazole.

Melting point: 152-155° C.
Elemental analysis for $C_{15}H_8N_2SCl_2$:

|  | C | H | N | S |
|---|---|---|---|---|
| Calculated: | 56.44% | 2.53% | 8.79% | 10.04% |
| Found: | 56.70% | 2.56% | 8.76% | 10.06% |

By following the above procedure, the following compounds were prepared.

EXAMPLE 87

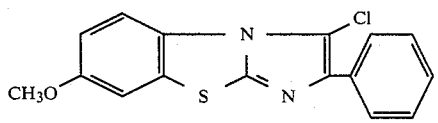

3-Chloro-7-methoxy-2-phenylimidazo[2,1-b]benzothiazole
melting point 180° C.
Elemental analysis for $C_{16}H_{11}N_2OSCl$:

|  | C (%) | H (%) | N (%) | S (%) |
|---|---|---|---|---|
| Calculated: | 60.28 | 3.48 | 8.79 | 11.31 |
| Found: | 60.25 | 3.51 | 8.80 | 11.22 |

EXAMPLE 88

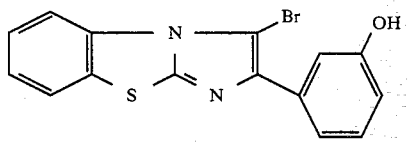

To 30 ml of chloroform were added 1.35 g of 2-(m-acetoxyphenyl)imidazo[2,1-b]benzothiazole and 0.94 g of N-bromosuccinimide and the mixture was stirred overnight at room temperature. The reaction mixture was concentrated under reduced pressure and the residue was washed with ether and dried to provide 2-(m-acetoxyphenyl)-3-bromoimidazo[2,1-b]benzothiazole. The product was suspended in 50 ml of methanol and after adding thereto 4 ml of 0.84 normal methanol solution of potassium hydroxide, the mixture was stirred for 30 minutes at room temperature. To the reaction mixture was added acetic acid to acidify the mixture and then 50 ml of water was added to the mixture to form crystals, which were recovered by filtration and recrystallized from a mixture of methylcellosolve and water to provide 1.2 g of 3-bromo-2-(m-hydroxyphenyl)imidazo[2,1-b]benzothiazole.

| Melting point: 218–220° C. | | | |
|---|---|---|---|
| Elemental analysis for $C_{15}H_9N_2BrOS$: | | | |
| | C (%) | H (%) | N (%) | Br (%) |
| Calculated: | 52.19 | 2.63 | 8.11 | 23.15 |
| Found: | 52.25 | 2.62 | 7.99 | 23.18 |

EXAMPLE 89

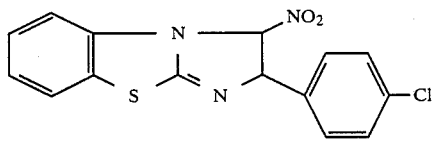

After cooling 30 ml of fuming nitric acid to −35° to −45° C., 3 g of 2-(p-chlorophenyl)imidazo[2,1-b]benzothiazole was gradually added thereto. The reaction mixture was poured into ice water and the crystals which formed were recovered by filtration and recrystallized from acetic acid to provide 2.2 g of 2-(p-chlorophenyl)-3-nitroimidazo[2,1-b]benzothiazole.

| Melting point: 180–183° C. | | |
|---|---|---|
| Elemental analysis for $C_{15}H_8O_2N_3SCl$: | | |
| | S (%) | Cl (%) |
| Calculated: | 9.72 | 10.75 |
| Found: | 9.53 | 10.75 |

EXAMPLE 90

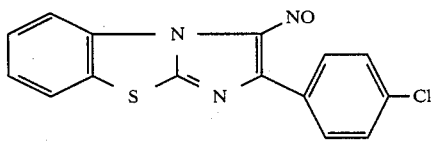

To 700 ml of acetic acid was added 14 g of 2-(p-chlorophenyl)imidazo[2,1-b]benzothiazole and after adding thereto 5 g of sodium nitrite with stirring at room temperature, the mixture was stirred for 3 hours. Thereafter, 500 ml of water was added to the mixture and the crystals thus formed were recovered by filtration and washed with water, then n-hexane, and further with 400 ml of chloroform to provide 10 g of 2-(p-chlorophenyl)-3-nitrosoimidazo[2,1-b]benzothiazole.
The product was recrystallized from chloroform to provide crystals having a melting point of 203°–206° C.

| Elemental analysis for $C_{15}H_8ON_3SCl$: | | | | |
|---|---|---|---|---|
| | C (%) | H (%) | N (%) | Cl (%) | S (%) |
| Calculated: | 57.42 | 2.57 | 13.39 | 11.30 | 10.22 |
| Found: | 57.34 | 2.42 | 13.26 | 11.48 | 10.29 |

EXAMPLE 91

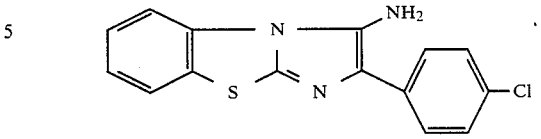

While suspending 9 g of 2-(p-chlorophenyl)-3-nitrosoimidazo[2,1-b]benzothiazole in 200 ml of acetic acid, 6 g of zinc powder was gradually added to the suspension at temperatures below 15° C. Insoluble materials were filtered away and 3 drops of concentrated sulfuric acid were added to the filtrate to form precipitates. After filtering away the precipitates, 20 ml of concentrated sulfuric acid was added to the mother liquor and the mixture was allowed to stand overnight. The crystals which formed were recovered by filtration and added to a mixture of ethyl acetate and water. After adding thereto potassium carbonate followed by stirring, the ethyl acetate layer which formed was recovered, washed with water, dried with anhydrous magnesium sulfate, and concentrated under reduced pressure to form crystals, which were recovered and recrystallized from toluene to provide 2.3 g of 3-amino-2-(p-chlorophenyl)imidazo[2,1-b]benzothiazole.

| Melting point: 193–196° C. (decompd.). | | | | |
|---|---|---|---|---|
| Elemental analysis for $C_{15}H_{10}N_3SCl$: | | | | |
| | C (%) | H (%) | N (%) | Cl (%) | S (%) |
| Calculated: | 60.10 | 3.36 | 14.02 | 11.83 | 10.69 |
| Found: | 60.42 | 3.24 | 13.99 | 12.01 | 10.87 |

EXAMPLE 92

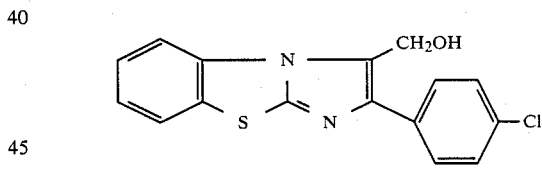

To a suspension of 2 g of 2-(p-chlorophenyl)-3-formylimidazo[2,1-b]benzothiazole in 100 ml of chloroform and 200 ml of ethanol was added 1 g of sodium borohydride and the mixture was stirred overnight at room temperature. The reaction mixture was concentrated under reduced pressure and 900 ml of chloroform was added to the residue. After removing the insoluble materials which formed, the residue was washed with water, dried with anhydrous magnesium sulfate, and concentrated under reduced pressure. The residue obtained was recrystallized from isopropyl alcohol to provide 1.2 g of 2-(p-chlorophenyl)-3-hydroxymethylimidazo[2,1-b]benzothiazole.

| Melting point: 218–220° C. | | | | |
|---|---|---|---|---|
| Elemental analysis for $C_{16}H_{11}N_2OSCl$: | | | | |
| | C (%) | H (%) | N (%) | S (%) | Cl (%) |
| Calculated: | 61.05 | 3.52 | 8.90 | 10.18 | 11.26 |
| Found: | 60.90 | 3.42 | 8.97 | 10.24 | 11.24 |

EXAMPLE 93

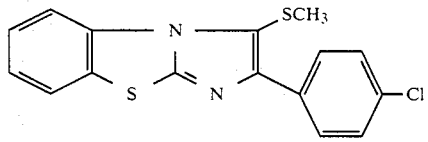

To a solution of 10 g of 2-(p-chlorophenyl-)imidazo[2,1-b]benzothiazole in 70 ml of methylene chloride was added dropwise a 1,1,2,2-tetrachloroethane solution of methylsulfinyl chloride obtained from 4 g of dimethyl disulfide and 5.2 g of sulfuryl chloride under ice cooling. Thereafter, the mixture was stirred overnight at room temperature. The reaction mixture was concentrated under reduced pressure and then the residue was extracted with 200 ml of chloroform. The extract was washed with an aqueous 5% sodium hydrogencarbonate solution and then water, dried with anhydrous magnesium sulfate, and concentrated under reduced pressure. The residue was recrystallized from methylcellosolve to provide 10.9 g of 2-(p-chlorophenyl)-3-methylthioimidazo[2,1-1]benzothiazole.

| Melting point: 190–192° C. Elemental analysis for $C_{16}H_{11}N_2S_2Cl$: | | | | | |
|---|---|---|---|---|---|
| | C (%) | H (%) | N (%) | S (%) | Cl (%) |
| Calculated: | 58.09 | 3.35 | 8.47 | 19.38 | 10.72 |
| Found: | 57.80 | 3.16 | 8.62 | 19.12 | 11.01 |

EXAMPLE 94

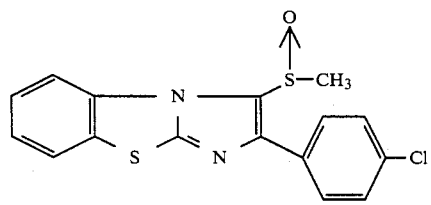

To a solution of 1.5 g of 2-(p-chlorophenyl)-3-methylthioimidazo[2,1-b]benzothiazole in 50 ml of chloroform was added 1.7 g of m-chloroperbenzoic acid and the mixture was stirred overnight at room temperature. The reaction mixture was washed with an aqueous 5% sodium hydrogencarbonate solution and then water, dried with anhydrous magnesium sulfate, and concentrated under reduced pressure. The residue was recrystallized from methylcellosolve to provide 1.25 g of 2-(p-chlorophenyl)-3-methylthiosulfinylimidazo[2,1-b]benzothiazole.

| Melting point: 185–187° C. (decompd.) Elemental analysis for $C_{16}H_{11}N_2S_2OCl$: | | | | | |
|---|---|---|---|---|---|
| | C (%) | H (%) | N (%) | Cl (%) | S (%) |
| Calculated: | 55.41 | 3.20 | 8.08 | 10.22 | 18.49 |
| Found: | 55.28 | 3.25 | 7.92 | 10.31 | 18.32 |

EXAMPLE 95

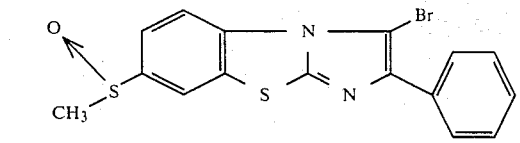

To 1.5 g of 7-methylthio-2phenylimidazo[2,1-b]benzothiazole were added 50 ml of chloroform and 20 ml of a saturated aqueous sodium hydrogencarbonate solution and while stirring vigorously, a solution of 1.6 g of bromine in 5 ml of chloroform was gradually added dropwise to the mixtue. Thereafter, the chloroform layer which formed was recovered, dried with anhydrous magnesium sulfate, and concentrated under reduced pressure. The residual solid materials were subjected to silica gel column chromatography and the product was eluted using a mixture of chloroform and ethyl acetate to provide 0.8 g of 3-bromo-7-methylsulfinyl-2-phenylimidazo[2,1-b]benzothiazole.

| Melting point: 206° C. Elemental analysis for $C_{16}H_{11}N_2OS_2Br$: | | | | |
|---|---|---|---|---|
| | C (%) | H (%) | N (%) | S (%) |
| Calculated: | 49.11 | 2.83 | 7.16 | 16.39 |
| Found: | 48.95 | 2.77 | 7.01 | 16.32 |

EXAMPLE 96

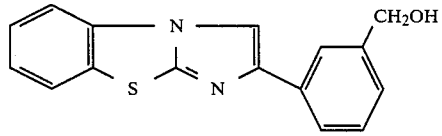

To a solution prepared by adding 0.2 g of lithium aluminum hydride to 20 ml of tetrahydrofuran cooled at 0°–5° C. was gradually added dropwise a solution of 1.2 g of 2-(m-methoxycarbonylphenyl)imidazo[2,1-b]benzothiazole in 10 ml of tetrahydrofuran and further the mixture was stirred for 10 minutes at 0°–5° C. After gradually adding 5 ml of 10% acetic acid to the reaction mixture, 50 ml of ethyl acetate was added to the mixture and the product was extracted. The extract was dried with anhydrous magnesium sulfate and concentrated to form 10 g of solid materials, which were recrystallized from isopropanol to provide 0.8 g of 2-(m-hydroxymethylphenyl)imidazo[2,1-b]benzothiazole.

| Melting point: 159° C. Elemental analysis for $C_{16}H_{12}N_2OS$: | | | | |
|---|---|---|---|---|
| | C (%) | H (%) | N (%) | S (%) |
| Calculated: | 68.55 | 4.31 | 9.99 | 11.44 |
| Found: | 68.36 | 4.30 | 10.07 | 11.56 |

By following the above procedure, the compound shown in the following example was prepared.

EXAMPLE 97

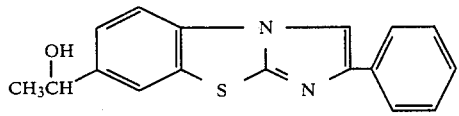

7-(1-Hydroxyethyl)-2-phenylimidazo[2,1-b]benzothiazole
Melting point: 132° C.
Elemental analysis for $C_{17}H_{14}N_2OS$:

|  | C | H | N | S |
|---|---|---|---|---|
| Calculated: | 69.36 | 4.79 | 9.52 | 10.89 |
| Found: | 69.20 | 5.01 | 9.49 | 10.75 |

By following the same procedure as in example 1, the following compounds were prepared.

EXAMPLE 98

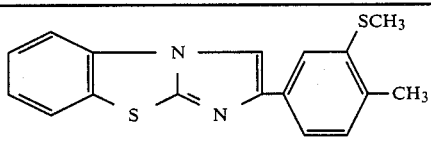

2-(4-Methyl-3-methylthiophenyl)imidazo[2,1-b]benzothiazole
melting point 130–132° C.
Elemental analysis for $C_{17}H_{14}N_2S_2$:

|  | C (%) | H (%) | N (%) | S (%) |
|---|---|---|---|---|
| Calculated: | 65.85 | 4.55 | 9.03 | 20.84 |
| Found: | 65.78 | 4.55 | 9.02 | 20.66 |

EXAMPLE 99

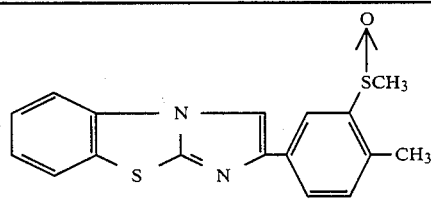

2-(4-Methyl-3-methylsulfinylphenyl)imidazo[2,1-b]benzothiazole
melting point 220–222° C.
Elemental analysis for $C_{17}H_{14}N_2OS_2$:

|  | C (%) | H (%) | N (%) | S (%) |
|---|---|---|---|---|
| Calculated: | 62.37 | 4.27 | 8.35 | 19.49 |
| Found: | 62.55 | 4.32 | 8.58 | 19.64 |

EXAMPLE 100

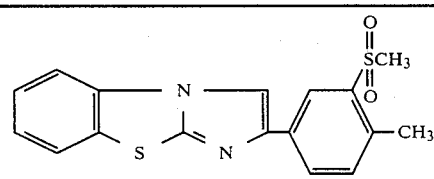

2-(4-Methyl-3-methylsulfonylphenyl)imidazo[2,1-b]benzothiazole
melting point 261–263° C.
Elemental analysis for $C_{17}H_{14}N_2O_2S_2$:

|  | C (%) | H (%) | N (%) | S (%) |
|---|---|---|---|---|
| Calculated: | 59.56 | 4.05 | 8.02 | 18.55 |

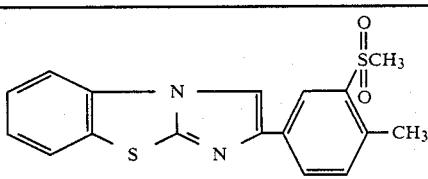

2-(4-Methyl-3-methylsulfonylphenyl)imidazo[2,1-b]benzothiazole
melting point 261–263° C.
Elemental analysis for $C_{17}H_{14}N_2O_2S_2$:

|  | C (%) | H (%) | N (%) | S (%) |
|---|---|---|---|---|
| Found: | 59.63 | 4.12 | 8.18 | 18.73 |

EXAMPLE 101

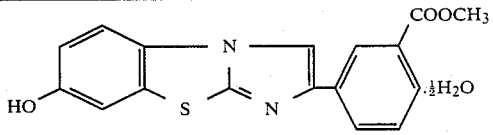

7-Hydroxy-2-(m-methoxycarbonylphenyl)imidazo[2,1-b]-benzothiazole hemihydrate
melting point 210–212° C.
Elemental analysis for $C_{17}H_{12}N_2O_3S \cdot \frac{1}{2}H_2O$

|  | C (%) | H (%) | N (%) | S (%) |
|---|---|---|---|---|
| Calculated: | 61.25 | 3.93 | 8.40 | 9.62 |
| Found: | 61.50 | 3.70 | 8.40 | 9.91 |

EXAMPLE 102

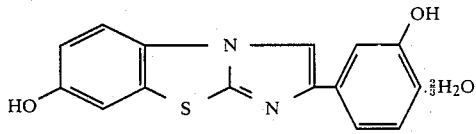

7-Hydroxy-2-(m-hydroxyphenyl)imidazo[2,1-b]benzothiazole
⅔hydrate
melting point 178–180° C.
Elemental analysis for $C_{15}H_{10}N_2O_2S \cdot \frac{2}{3}H_2O$:

|  | C (%) | H (%) | N (%) | S (%) |
|---|---|---|---|---|
| Calculated: | 61.21 | 3.88 | 9.52 | 10.89 |
| Found: | 61.36 | 3.81 | 9.35 | 10.61 |

By following the same procedure as in example 75, following compound was prepared.

EXAMPLE 103

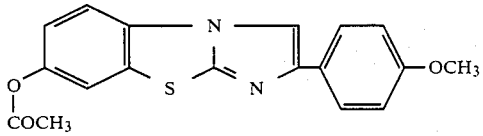

7-Acetoxy-2-(p-methoxyphenyl)imidazo[2,1-b]benzothiazole
melting point 215° C.
Elemental analysis for $C_{18}H_{14}N_2O_3S$:

|  | C (%) | H (%) | N (%) | S (%) |
|---|---|---|---|---|
| Calculated: | 63.89 | 4.17 | 8.28 | 9.47 |
| Found: | 63.95 | 4.03 | 8.23 | 9.52 |

By following the same procedure as in example 60, following compound was prepared.

EXAMPLE 104

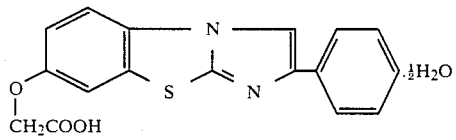

7-Carboxymethyloxy-2-phenylimidazo[2,1-b]benzothiazole hemihydrate melting point 240–243° C.

Elemental analysis for $C_{17}H_{12}N_2O_3S.\frac{1}{2}H_2O$

|  | C (%) | H (%) | N (%) | S (%) |
|---|---|---|---|---|
| Calculated: | 61.25 | 3.93 | 8.40 | 9.62 |
| Found: | 61.42 | 3.96 | 8.15 | 9.36 |

EXAMPLE 105

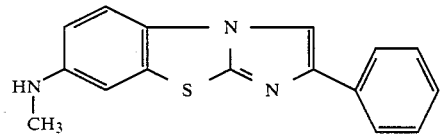

To 50 ml of ethanol were added 500 mg of 7-amino-2-phenylimidazo[2,1-b]benzothiazole, 265 mg of methyl iodide and 260 mg of potassium carbonate anhydride and while stirring vigorously, the mixture was refluxed for 2 days. The reaction mixture was cooled and then concentrated under reduced pressure. The residue was extracted with 50 ml of ethyl acetate and the extract was washed with water, dried with anhydrous magnesium sulfate, and then the extract was concentrated under reduced pressure. The residue was subjected to silica gel column chromatography (eluant: toluene:ethyl acetate=4:1) and the obtained crystals were recrystallized from toluene to provide 50 mg of 7-methylamino-2-phenylimidazo-[2,1-b]benzothiazole.

Melting point: 175–176° C.
Elemental analysis for $C_{16}H_{13}N_3S$:

|  | C (%) | H (%) | N (%) | S (%) |
|---|---|---|---|---|
| Calculated: | 68.79 | 4.69 | 15.04 | 11.48 |
| Found: | 68.85 | 4.57 | 14.93 | 11.59 |

EXAMPLE 106

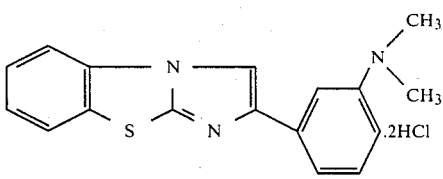

To 50 ml of methylethylketone were added 2.6 g of 2-(m-aminophenyl)imidazo[2,1-b]benzothiazole, 2.8 g of methyl iodide and 2.8 g of potassium carbonate and the mixture was refluxed for 2 hours. The insoluble materials were then filtered off and the filtrate was concentrated under reduced pressure. The residue was mixed with 50 ml of water and extracted with 50 ml of ethyl acetate. The ethyl acetate layer formed was recovered, dried by anhydrous magnesium sulfate, and then solvent was distilled off to provide oily product. The oily product was dissolved in 20 ml of 1N hydrochloric acid ethanol and 20 ml of ether was added to the solution, and then white crystals formed were recovered by filtration to provide 2.0 g of 2-[m-(N,N-dimethyl)-phenyl]imidazo[2,1-b]benzothiazole dihydrochloride.

Melting point: 218–220° C.
Elemental analysis for $C_{17}H_{17}N_3SCl_2$:

|  | C (%) | H (%) | N (%) | Cl (%) |
|---|---|---|---|---|
| Calculated: | 55.74 | 4.68 | 11.48 | 19.36 |
| Found: | 55.89 | 4.91 | 11.17 | 19.06 |

What is claimed is:

1. A compound of the formula

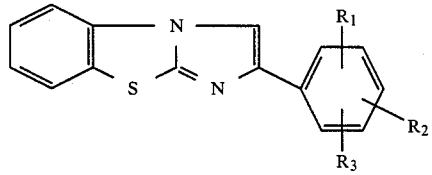

wherein $R_1$ is hydroxy, nitro or methoxycarbonyl, $R_2$ is hydroxy, chloro or hydrogen and $R_3$ is chloro or hydrogen wherein when $R_1$ is nitro or methoxycarbonyl $R_2$ and $R_3$ are hydrogen and wherein when $R_1$ and $R_2$ are hydroxy $R_3$ is hydrogen.

2. 2-(m-Hydroxyphenyl)imidazo[2,1-b]benzothiazole.
3. 2-(o-Hydroxyphenyl)imidazo[2,1-b[benzothiazole.
4. 2-(p-Hydroxyphenyl)imidazo[2,1-b]benzothiazole.
5. 2-(m-Nitrophenyl)imidazo[2,1-b]benzothiazole.
6. 2-(m-Methoxycarbonylphenyl)imidazo[2,1-b]benzothiazole.
7. 2-(3-Chloro-4-hydroxyphenyl)imidazo[2,1-b]benzothiazole.
8. 2-(3,5-Dichloro-4-hydroxyphenyl)imidazo[2,1-b]benzothiazole.
9. 7-Hydroxy-2-(p-hydroxyphenyl)imidazo[2,1-b]benzothiazole.
10. A compound of claim 1 wherein $R_1$ is hydroxy and $R_2$ is hydrogen or chloro.
11. A compound of claim 10 wherein $R_1$ is hydroxy and $R_2$ and $R_3$ are hydrogen.

* * * * *